US010059999B2

(12) United States Patent
Jia et al.

(10) Patent No.: US 10,059,999 B2
(45) Date of Patent: Aug. 28, 2018

(54) MOLECULAR MARKERS ASSOCIATED WITH SOYBEAN TOLERANCE TO LOW IRON GROWTH CONDITIONS

(71) Applicant: Monsanto Technology LLC, St. Louis, MO (US)

(72) Inventors: Hongwu Jia, Grover, MO (US); Bradley La Vallee, Clarkson Valley, MO (US); Roger L. Lussenden, Grover, MO (US); Jennifer L. Yates, St. Louis, MO (US); Xianghai Ye, Ankeny, IA (US)

(73) Assignee: Monsanto Technology LLC, St. Louis, MI (US)

( * ) Notice: Subject to any disclaimer, the term of this patent is extended or adjusted under 35 U.S.C. 154(b) by 331 days.

(21) Appl. No.: 14/300,384

(22) Filed: Jun. 10, 2014

(65) Prior Publication Data
US 2014/0366214 A1    Dec. 11, 2014

Related U.S. Application Data

(60) Provisional application No. 61/833,129, filed on Jun. 10, 2013.

(51) Int. Cl.
C12Q 1/68      (2018.01)
A01H 1/04      (2006.01)
C12N 15/82     (2006.01)
C12Q 1/6895    (2018.01)

(52) U.S. Cl.
CPC ............ *C12Q 1/6895* (2013.01); *A01H 1/04* (2013.01); *C12Q 2600/13* (2013.01); *Y10T 436/143333* (2015.01)

(58) Field of Classification Search
None
See application file for complete search history.

(56) References Cited

U.S. PATENT DOCUMENTS

| | | |
|---|---|---|
| 4,582,788 A | 4/1986 | Erlich |
| 4,683,194 A | 7/1987 | Saiki et al. |
| 4,683,202 A | 7/1987 | Mullis |
| 4,971,908 A | 11/1990 | Kishore et al. |
| 5,188,642 A | 2/1993 | Shah et al. |
| 5,210,015 A | 5/1993 | Gelfand et al. |
| 5,217,863 A | 6/1993 | Cotton et al. |
| 5,468,613 A | 11/1995 | Erlich et al. |
| 5,595,890 A | 1/1997 | Newton et al. |
| 5,616,464 A | 4/1997 | Albagli et al. |
| 5,762,876 A | 6/1998 | Lincoln et al. |
| 5,776,760 A | 7/1998 | Barry et al. |
| 5,800,944 A | 9/1998 | Blonsky et al. |
| 5,876,930 A | 3/1999 | Livak et al. |
| 5,945,283 A | 8/1999 | Kwok et al. |
| 6,004,744 A | 12/1999 | Goelet et al. |
| 6,013,431 A | 1/2000 | Söderlund et al. |
| 6,030,787 A | 2/2000 | Livak et al. |
| 6,090,558 A | 7/2000 | Butler et al. |
| 6,207,367 B1 | 3/2001 | Helentjaris et al. |
| 6,225,114 B1 | 5/2001 | Eichholtz et al. |
| 6,399,855 B1 | 6/2002 | Beavis |
| 6,503,710 B2 | 1/2003 | Gut et al. |
| 6,613,509 B1 | 9/2003 | Chen |
| 6,799,122 B2 | 9/2004 | Benson |
| 6,803,501 B2 | 10/2004 | Baerson et al. |
| 6,913,879 B1 | 7/2005 | Schena |
| RE38,825 E | 10/2005 | Barry et al. |
| 6,959,617 B2 | 11/2005 | Deppermann |
| 6,996,476 B2 | 2/2006 | Najarian |
| RE39,247 E | 8/2006 | Barry et al. |
| 7,134,351 B2 | 11/2006 | Deppermann |
| 7,238,476 B2 | 7/2007 | McKeown et al. |
| 7,250,252 B2 | 7/2007 | Katz et al. |
| 7,270,981 B2 | 9/2007 | Armes et al. |
| 7,282,355 B2 | 10/2007 | Shi |
| 7,297,485 B2 | 11/2007 | Bornarth et al. |
| 7,312,039 B2 | 12/2007 | Barany et al. |
| 7,454,989 B2 | 11/2008 | Deppermann |
| 7,502,113 B2 | 3/2009 | Deppermann et al. |
| 7,582,806 B2 | 9/2009 | Sebastian et al. |
| 7,591,101 B2 | 9/2009 | Deppermann |
| 7,611,842 B2 | 11/2009 | Deppermann et al. |

(Continued)

FOREIGN PATENT DOCUMENTS

EP    0 050 424 A1    4/1982
EP    0 084 796 A2    8/1983
(Continued)

OTHER PUBLICATIONS

Wang et al., 2008, Theor. Appl. Genet. 116: 777-787.*
O'Rourke, 2008, PhD Thesis, University of Iowa, pp. 1-191.*
O'Rourke et al., 2009, BMC Genomics 10: 376, with Additional files. 4 and 6.*
Funke et al., 1993, Plant Molecular Biology 22: 437-446.*
Batley and Edwards, 2007, In; Association Mapping in Plants, pp. 95-102.*
Borevitz et al., "Large-Scale Identification of Single-Feature Polymorphisms in Complex Genomes," *Genome Res.*, 13:513-523 (2003).

(Continued)

*Primary Examiner* — Amjad Abraham
*Assistant Examiner* — Bratislav Stankovic
(74) *Attorney, Agent, or Firm* — Lawrence J. Lavin, Jr.; Arnold & Porter Kaye Scholer LLP

(57) ABSTRACT

The present invention provides methods and compositions for identifying soybean plants that are tolerant or have improved tolerance, or those that are susceptible to, iron deficient growth conditions. The methods use molecular markers to identify, select, and/or introgress genetic loci modulating phenotypic expression of an iron deficiency tolerance trait in soybean plant breeding. Methods are provided for screening germplasm entries for the performance and expression of this trait.

8 Claims, No Drawings
Specification includes a Sequence Listing.

(56) References Cited

U.S. PATENT DOCUMENTS

| | | |
|---|---|---|
| 7,666,644 B2 | 2/2010 | Castle et al. |
| 7,685,768 B2 | 3/2010 | Deppermann |
| 7,977,533 B2 | 7/2011 | Sebastian et al. |
| 2005/0015827 A1 | 1/2005 | Podlich et al. |
| 2005/0204780 A1 | 9/2005 | Moridaira et al. |
| 2005/0216545 A1 | 9/2005 | Aldrich et al. |
| 2005/0218305 A1 | 10/2005 | Tsukamoto et al. |
| 2006/0042527 A1 | 3/2006 | Deppermann |
| 2006/0046244 A1 | 3/2006 | Deppermann |
| 2006/0046264 A1 | 3/2006 | Deppermann et al. |
| 2006/0048247 A1 | 3/2006 | Deppermann |
| 2006/0048248 A1 | 3/2006 | Deppermann |
| 2007/0204366 A1 | 8/2007 | Deppermann et al. |
| 2007/0207485 A1 | 9/2007 | Deppermann et al. |
| 2009/0025288 A1 | 1/2009 | Deppermann et al. |
| 2009/0036308 A1 | 2/2009 | Guida, Jr. et al. |
| 2009/0215060 A1 | 8/2009 | Deppermann et al. |
| 2010/0086963 A1 | 4/2010 | Deppermann et al. |
| 2010/0099859 A1 | 4/2010 | Malven et al. |

FOREIGN PATENT DOCUMENTS

| | | |
|---|---|---|
| EP | 0 201 184 A2 | 12/1986 |
| EP | 0 237 362 A1 | 9/1987 |
| EP | 0 258 017 A2 | 3/1988 |

OTHER PUBLICATIONS

Charlson et al., "Associating SSR Markers with Soybean Resistance to Iron Chlorosis," *Journal of Plant Nutrition*, 26(10-11):2267-2276 (2003).

Choi et al., "A Soybean Transcript Map: Gene Distribution, Haplotype and Single-Nucleotide Polymorphism Analysis," *Genetics.*, 176(1):685-696 (2007).

Cox et al., "Relationship Between Coefficient of Parentage and Genetic Similarity Indices in the Soybean," *Crop Science*, 25:529-532 (1985).

Cui et al., "Detecting single-feature polymorphisms using oligonucleotide arrays and robustified projection pursuit," *Bioinformatics*, 21:3852-3858 (2005).

Dahiya et al., "Effect of Salinity, Alkalinity and Iron Sources on Availability of Iron," *Plant and Soil*, 51:13-18 (1979).

Diers et al., "Possible Identification of Quantitative Trait Loci Affecting Iron Efficiency in Soybean," *Journal of Plant Nutrition*, 15(10):2127-2136 (1992).

Gonzalez-Vallejo et al. "Iron Deficiency Decreases the Fe(III)-Chelate Reducing Activity of Leaf Protoplasts," *Plant Physiol.*, 122(2):337-344 (2000).

Goos et al., "A Comparison of Three Methods for Reducing Iron-Deficiency Chlorosis in Soybean," *Agronomy Journal*, 92:1135-1139 (2000).

Goos et al., "Seed Treatment, Seeding Rate, and Cultivar Effects on Iron Deficiency Chlorosis of Soybean," *Journal of Plant Nutrition*, 24(8):1255-1268 (2001).

Hintz et al., "Population Development for the Selection of High-Yielding Soybean Cultivars with Resistance to Iron Deficiency Chlorosis," *Crop Science*, 27:707-710 (1987).

Karkosh et al., "Seed Treatment for Control of Iron-Deficiency Chlorosis of Soybean," *Crop Science*, 28:369-370 (1988).

Lin et al., "Molecular Characterization of Iron Deficiency Chlorosis in Soybean," *Journal of Plant Nutrition*, 23:1929-1939 (2000).

Mullis et al., "Specific Enzymatic Amplification of DNA in Vitro: The Polymerase Chain Reaction," *Cold Spring Harbor Symp. Quant. Biol.*, 51:263-273 (1986).

Padgette et al., "Development, Identification, and Characterization of a Glyphosate-Tolerant Soybean Line," *Crop Sci.* 35:1451-1461 (1995).

Service, "The Race for the $1000 Genome," *Science*, 311:1544-1546 (2006).

Hard et al., "Genetics Principles and Analysis," *Jones and Bartlett publishers*, 4:128 (1998).

* cited by examiner

MOLECULAR MARKERS ASSOCIATED WITH SOYBEAN TOLERANCE TO LOW IRON GROWTH CONDITIONS

CROSS REFERENCE TO RELATED APPLICATION

This application claims the benefit of priority to U.S. Provisional Application Ser. No. 61/833,129 filed Jun. 10, 2013.

INCORPORATION OF SEQUENCE LISTING

A sequence listing containing the file named "46-21-59627.txt" which is 99,843 bytes (measured in MS-Windows®) and created on May 30, 2014, comprises "147" nucleotide sequences, is provided herewith via the USPTO's EFS system and is herein incorporated by reference in its entirety.

BACKGROUND OF INVENTION

Soybean, *Glycine max* (L.) Merril, is a major economic crop worldwide and is a primary source of vegetable oil and protein (Sinclair and Backman, Compendium of Soybean Diseases, 3rd Ed. APS Press, St. Paul, Minn., p. 106. (1989). Growing demand for low cholesterol and high fiber diets has increased soybean's importance as a health food.

Soybean varieties grown in the United States have a narrow genetic base. Six introductions, 'Mandarin,' 'Manchu,' 'Mandarin' (Ottawa), 'Richland,' 'AK' (Harrow), and 'Mukden,' contributed nearly 70% of the germplasm represented in 136 cultivar releases. To date, modern day cultivars can be traced back from these six soybean strains from China. In a study conducted by Cox et al., Crop Sci. 25:529-532 (1988), the soybean germplasm is comprised of 90% adapted materials, 9% un-adapted, and only 1% from exotic species. The genetic base of cultivated soybean could be widened through exotic species. In addition, exotic species may possess such key traits as disease, stress, and insect resistance.

The availability of a specific micronutrient, such as iron (Fe), is often related to soil characteristics. Soil pH has a major impact on the availability of Fe. Iron deficiency has been a common, serious, and yield-limiting problem for soybean production in some parts of the United States.

Iron is one of the necessary micronutrients for soybean plant growth and development. It is also needed for the development of chlorophyll. Iron is involved in energy transfer, plant respiration, and plant metabolism. It is also a constituent of certain enzymes and proteins in plants. Iron is necessary for soybean root nodule formation and plays a role in N-fixation; thus, low levels of Fe can lead to reduced nitrogen content and poor yield.

When iron is limited, soybean plants can develop iron deficiency chlorosis (IDC). Soybean IDC is the result of a complex interaction among many factors including soil chemistry, environmental conditions, and soybean physiology and genetics. The most common IDC symptom is interveinal chlorosis in which leaf tissue of newly developed soybean leaves turn yellow, while the veins remain green. The leaves may develop necrotic spots that eventually coalesce and fall off the plant. Iron deficiency symptoms are similar to that of Manganese (Mn) deficiency; therefore, only soil and tissue analysis can distinguish the two micronutrient deficiencies.

Severe yield reductions due to IDC have been reported throughout the North-Central U.S with losses estimated to be around $120 million annually. In some instances, yield loss can be greater than 50%. Typically, soybean IDC symptoms occur between the first and third trifoliate stage, so under less-severe iron deficiency conditions, symptoms may improve later in the season.

Soybean plants grown in calcareous soils with a pH of greater than 7.4 or in heavy, poorly drained, and compacted soils may exhibit IDC symptoms due to insufficient iron uptake. However, soil pH is not a good indicator and does not correlate very well with IDC. Symptoms are highly variable between years and varieties and depend on other soil factors and weather conditions.

There is, however, a direct relationship between IDC incidence and concentrations of calcium carbonate and soluble salts. Iron uptake is adversely impacted by high concentrations of phosphorous (P), manganese (Mn), and zinc (Zn). Moreover, high levels of calcium (Ca) in the soil cause Fe molecules to bind tightly to the soil particles, making them unavailable for uptake. Therefore it is important to monitor the levels of calcium carbonate and soluble salts in the soil. Sandy soils with low organic matter may also lead to a greater incidence of IDC symptoms.

Weather also plays a role in IDC symptoms. Cool soil temperature and wet weather, combined with marginal levels of available Fe in the soil can increase IDC symptoms.

Soybean producers have sought to develop plants tolerant to low iron growth conditions (thus not exhibiting IDC) as a cost-effective alternative or supplement to standard foliar, soil and/or seed treatments (e.g., Hintz et al. (1987) "Population development for the selection of high-yielding soybean cultivars with resistance to iron deficiency chlorosis," Crop Sci. 28:369-370). Studies also suggest that cultivar selection is more reliable and universally applicable than foliar sprays or iron seed treatment methods, though environmental and cultivar selection methods can also be used effectively in combination (Goos and Johnson (2000) "A Comparison of Three Methods for Reducing Iron-Deficiency Chlorosis in Soybean" Agronomy Journal 92:1135-1139; and Goos and Johnson "Seed Treatment, Seeding Rate, and Cultivar Effects on Iron Deficiency Chlorosis of Soybean" Journal of Plant Nutrition 24 (8) 1255-1268).

Soybean cultivar improvement for IDC tolerance can be performed using classical breeding methods, or, more preferably, using marker assisted selection (MAS). Genetic markers for low iron growth condition tolerance/susceptibility have been identified (e.g., Lin et al. (2000) "Molecular characterization of iron deficiency chlorosis in soybean" Journal of Plant Nutrition 23:1929-1939). Recent work suggests that marker assisted selection is particularly beneficial when selecting plants because the strength of environmental effects on chlorosis expression impedes progress in improving tolerance. See also, Charlson et al., "Associating SSR Markers with Soybean Resistance to Iron Chlorosis," Journal of Plant Nutrition, vol. 26, nos. 10 & 11; 2267-2276 (2003). U.S. Pat. Nos. 7,977,533 and 7,582,806 disclose genetic loci associated with iron deficiency tolerance in soybean.

There is a need in the art of plant breeding to identify additional markers linked to genomic regions associated with tolerance to low iron growth conditions (e.g., IDC tolerance) in soybean. There is, in particular, a need for numerous markers that are closely associated with low iron growth condition tolerance in soybean that permit introgression of such regions in the absence of extraneous linked DNA from the source germplasm containing the regions.

Additionally, there is a need for rapid, cost-efficient methods to assay the absence or presence of IDC tolerance loci in soybean.

SUMMARY OF INVENTION

The present invention provides for methods of creating a population of soybean plants with a low iron growth condition tolerant phenotype, comprising a.) providing a first population of soybean plants; b.) detecting in said soybean plant an allele in at least one polymorphic nucleic acid marker locus associated with the low iron growth condition tolerant phenotype wherein the marker locus genetically linked by less than 20 cM to a linkage group J genomic region flanked by loci ASMBL_10470 and TC370075, linkage group E genomic region flanked by loci DB975811 and GLYMA15G06010, linkage group M genomic region flanked by loci TA75172_3847 and TC380682, linkage group D2 genomic region flanked by loci TC350035 and Gm_W82_CR17.G8870, or linkage group O genomic region flanked by loci NA and Cf16144d; c.) selecting said plant containing said allele to provide a plant having a genotype associated with a low iron growth condition tolerant phenotype; and d.) producing a population of offspring from at least on of said selected soybean plants.

In some embodiments of the invention, the marker locus is genetically linked by less than 15 cM to the linkage group J genomic region flanked by loci ASMBL_10470 and TC370075, linkage group E genomic region flanked by loci DB975811 and GLYMA15G06010, linkage group M genomic region flanked by loci TA75172_3847 and TC380682, linkage group D2 genomic region flanked by loci TC350035 and Gm_W82_CR17.G8870, or linkage group O genomic region flanked by loci NA and Cf16144d.

In some embodiments of the invention, the marker locus is genetically linked by less than 10 cM to the linkage group J genomic region flanked by loci ASMBL_10470 and TC370075, linkage group E genomic region flanked by loci DB975811 and GLYMA15G06010, linkage group M genomic region flanked by loci TA75172_3847 and TC380682, linkage group D2 genomic region flanked by loci TC350035 and Gm_W82_CR17.G8870, or linkage group O genomic region flanked by loci NA and Cf16144d.

In some embodiments of the invention a second marker locus associated with the low iron growth condition tolerant phenotype is in linkage group J genomic region flanked by loci ASMBL_10470 and TC370075.

In some embodiments of the invention a second marker locus associated with the low iron growth condition tolerant phenotype is in linkage group E genomic region flanked by loci DB975811 and GLYMA15G06010.

In some embodiments of the invention a second marker locus associated with the low iron growth condition tolerant phenotype is in linkage group M genomic region flanked by loci TA75172_3847 and TC380682.

In some embodiments of the invention a second marker locus associated with the low iron growth condition tolerant phenotype is in linkage group D2 genomic region flanked by loci TC350035 and Gm_W82_CR17.G8870.

In some embodiments of the invention a second marker locus associated with the low iron growth condition tolerant phenotype is in linkage group O genomic region flanked by loci NA and Cf16144d.

Also provided herein are methods for creating a population of soybean plants comprising at least one allele associated with the low iron growth phenotype comprising at least one of SEQ ID NOs: 1-147. In certain embodiments, these methods comprise a.) genotyping a first population of soybean plants, said population containing at least one allele associated with the low iron growth condition tolerant phenotype, the at least one allele associated with the low iron growth condition tolerant phenotype comprising at least one of SEQ ID NOS 1-147; b.) selecting from said first population one or more identified soybean plants containing said at least one allele associated with the low iron growth condition tolerant phenotype comprising at least one of SEQ ID NOS 1-147; and c.) producing from said selected soybean plants a second population, thereby creating a population of soybean plants comprising at least one allele associated with the low iron growth condition tolerant phenotype comprising at lest one of SEQ ID NOS 1-147.

Further areas of applicability will become apparent from the description provided herein. It should be understood that the description and specific examples are intended for purposes of illustration only and are not intended to limit the scope of the present disclosure.

DESCRIPTION OF INVENTION

I. Definitions

Unless otherwise indicated herein, nucleic acid sequences are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains.

As used herein, an "allele" refers to one of two or more alternative forms of a genomic sequence at a given locus on a chromosome. When all the alleles present at a given locus on a chromosome are the same, that plant is homozygous at that locus. If the alleles present at a given locus on a chromosome differ, that plant is heterozygous at that locus.

As used herein, the term "bulk" refers to a method of managing a segregating population during inbreeding that involves growing the population in a bulk plot, harvesting the self-pollinated seed of plants in bulk, and using a sample of the bulk to plant the next generation.

As used herein, the term "comprising" means "including but not limited to".

As used herein, the term "locus" refers to a position on a genomic sequence that is usually found by a point of reference; e.g., a short DNA sequence that is a gene, or part of a gene or intergenic region. A locus may refer to a nucleotide position at a reference point on a chromosome, such as a position from the end of the chromosome.

As used herein, "linkage group J" corresponds to the soybean linkage group J described in Choi, et al., Genetics. 2007 May; 176(1): 685-696. Linkage group J, as used herein, also corresponds to soybean chromosome 16 (as described on the World Wide Web at soybase.org/LG2Xsome.php).

As used herein, "linkage group E" corresponds to the soybean linkage group E described in Choi, et al., Genetics. 2007 May; 176(1): 685-696. Linkage group E, as used herein, also corresponds to soybean chromosome 15 (as described on the World Wide Web at soybase.org/LG2Xsome.php).

As used herein, "linkage group M" corresponds to the soybean linkage group M described in Choi, et al., Genetics. 2007 May; 176(1): 685-696. Linkage group M, as used herein, also corresponds to soybean chromosome 7 (as described on the World Wide Web at soybase.org/LG2Xsome.php).

As used herein, "linkage group D2" corresponds to the soybean linkage group D2 described in Choi, et al., Genetics. 2007 May; 176(1): 685-696. Linkage group D2, as used herein, also corresponds to soybean chromosome 17 (as described on the World Wide Web at soybase.org/LG2Xsome.php).

As used herein, "linkage group O" corresponds to the soybean linkage group O described in Choi, et al., Genetics. 2007 May; 176(1): 685-696. Linkage group O, as used herein, also corresponds to soybean chromosome 10 (as described on the World Wide Web at soybase.org/LG2Xsome.php).

As used herein, "polymorphism" means the presence of one or more variations of a nucleic acid sequence at one or more loci in a population of at least two members. The variation can comprise, but is not limited to, one or more nucleotide base substitutions, the insertion of one or more nucleotides, a nucleotide sequence inversion, and/or the deletion of one or more nucleotides.

As used herein, "genotype" means the genetic component of the phenotype and it can be indirectly characterized using markers or directly characterized by nucleic acid sequencing.

As used herein, the term "introgressed," when used in reference to a genetic locus, refers to a genetic locus that has been introduced into a new genetic background. Introgression of a genetic locus can thus be achieved through both plant breeding methods or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion. In certain embodiments, introgression could thus be achieved by substitution of a locus not associated with tolerance to low iron growth conditions with a corresponding locus that is associated with low iron growth condition tolerance or by conversion of a locus from a non-tolerant genotype to a tolerant genotype.

As used herein, "linkage" refers to relative frequency at which types of gametes are produced in a cross. For example, if locus A has genes "A" or "a" and locus B has genes "B" or "b," then a cross between parent 1 with AABB and parent 2 with aabb can produce four possible gametes segregating into AB, Ab, aB and ab genotypes. The null expectation is that there will be independent equal segregation into each of the four possible genotypes, i.e. no linkage between locus A and locus B results in ¼ of the gametes from each genotype (AB, Ab, aB, and ab). Segregation of gametes into genotype ratios differing from ¼ indicates linkage between locus A and locus B. As used herein, linkage can be between two markers, or alternatively between a marker and a phenotype. A marker locus can be associated with (linked to) a trait, e.g., a marker locus can be associated with tolerance or improved tolerance to a plant pathogen when the marker locus is in linkage disequilibrium (LD) with the tolerance trait. The degree of linkage of a molecular marker to a phenotypic trait (e.g., a QTL) is measured, e.g., as a statistical probability of co-segregation of that molecular marker with the phenotype.

As used herein, the linkage relationship between a molecular marker and a phenotype is given is the statistical likelihood that the particular combination of a phenotype and the presence or absence of a particular marker allele is random. Thus, the lower the probability score, the greater the likelihood that a phenotype and a particular marker will cosegregate. In some embodiments, a probability score of 0.05 ($p=0.05$, or a 5% probability) of random assortment is considered a significant indication of co-segregation. However, the present invention is not limited to this particular standard, and an acceptable probability can be any probability of less than 50% ($p<0.5$). For example, a significant probability can be less than 0.25, less than 0.20, less than 0.15, or less than 0.1.

As used herein, the term "linked" or "genetically linked," when used in the context of markers and/or genomic regions, means that recombination between two linked loci occurs with a frequency of equal to or less than about 10% (i.e., are separated on a genetic map by not more than 10 cM). In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 20, 19, 18, 17, 16, 15, 14, 13, 12, 11, 10, 9, 8, 7, 6, 5, 4, 3, 2, 1, 0.75, 0.5 or 0.25 cM or less from each other.

As used herein, "marker," "genetic marker," "molecular marker," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus.

As used herein, "marker assay" means a method for detecting a polymorphism at a particular locus using a particular method. Marker assays thus include, but are not limited to, measurement of at least one phenotype (such as disease resistance, seed color, flower color, or other visually detectable trait as well as any biochemical trait), restriction fragment length polymorphism (RFLP), single base extension, electrophoresis, sequence alignment, allelic specific oligonucleotide hybridization (ASO), random amplified polymorphic DNA (RAPD), microarray-based polymorphism detection technologies, and the like.

As used herein, "phenotype" means the detectable characteristics of a cell or organism which can be influenced by gene expression.

As used herein, a "nucleic acid molecule," of naturally occurring origins or otherwise, may be an "isolated" nucleic acid molecule. An isolated nucleic acid molecule is one removed from its native cellular and chromosomal environment. The term "isolated" is not intended to encompass molecules present in their native state. If desired, an isolated nucleic acid may be substantially purified, meaning that it is the predominant species present in a preparation. A substantially purified molecule may be at least about 60% free, preferably at least about 75% free, more preferably at least about 90% free, and most preferably at least about 95% free from the other molecules (exclusive of solvent) present in the preparation.

As used herein, "quantitative trait locus (QTL)" means a genetic domain that effects a phenotype that can be described in quantitative terms and can be assigned a "phenotypic value" which corresponds to a quantitative value for the phenotypic trait. A QTL can act through a single gene mechanism or by a polygenic mechanism. In some aspects, the invention provides QTL genomic regions, where a QTL (or multiple QTLs) that segregates with low iron tolerance is contained in those regions. In one embodiment of this invention, the boundaries of genomic regions are drawn to encompass markers that will be linked to one or more QTL. In other words, the chromosome interval is drawn such that any marker that lies within that region (including the terminal markers that define the boundaries of the region) is genetically linked to the QTL. Each region comprises at least one QTL, and furthermore, may indeed comprise more than one QTL. Close proximity of multiple QTL in the same region may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the invention.

As used herein, the term "soybean" means *Glycine max* and includes all plant varieties that can be bred with soybean, including wild soybean species. In certain embodiments, soybean plants from the species *Glycine max* and the subspecies *Glycine max* L. ssp. *max* or *Glycine max* ssp. *formosana* can be genotyped using the compositions and methods of the present invention. In an additional aspect, the soybean plant is from the species *Glycine soja*, otherwise known as wild soybean, can be genotyped using these compositions and methods. Alternatively, soybean germplasm derived from any of *Glycine max*, *Glycine max* L. ssp. *max*, *Glycine max* ssp. *Formosana*, and/or *Glycine soja* can be genotyped using compositions and methods provided herein.

As used herein, the term "single nucleotide polymorphism," also referred to by the abbreviation "SNP," means a polymorphism at a single site wherein the polymorphism constitutes any or all of a single base pair change, an insertion of one or more base pairs, and/or a deletion of one or more base pairs.

As used herein, the phrases "low iron," "low-available iron," "low soluble iron," "low iron conditions," "low iron growth conditions," "iron shortage" or "iron deficiency" or the like refer to conditions where iron availability is less than optimal for soybean growth, and can cause plant pathology, e.g., IDC, due to the lack of metabolically-available iron. It is recognized that under "iron deficient" conditions, the absolute concentration of atomic iron may be sufficient, but the form of the iron (e.g., its incorporation into various molecular structures) and other environmental factors may make the iron unavailable for plant use. For example, high carbonate levels, high pH, high salt content, herbicide applications, cool temperatures, saturated soils, or other environmental factors can decrease iron solubility, and reduce the solubilized forms of iron that the plant requires for uptake. One of skill in the art is familiar with assays to measure iron content of soil, as well as those concentrations of iron that are optimal or sub-optimal for plant growth.

As used herein, the terms "tolerance" or "improved tolerance" in reference to a soybean plant grown in low iron growth conditions is an indication that the soybean plant is less affected by the low-available iron conditions with respect to yield, survivability and/or other relevant agronomic measures, compared to a less tolerant, more "susceptible" plant. Tolerance is a relative term, indicating that a tolerant" plant survives and/or produces better yield of soybean in low-available iron growth conditions compared to a different (less tolerant) plant (e.g., a different soybean strain) grown in similar low-available iron conditions. That is, the low-available iron growth conditions cause a reduced decrease in soybean survival and/or yield in a tolerant soybean plant, as compared to a susceptible soybean plant. As used in the art, iron-deficiency "tolerance" is sometimes used interchangeably with iron-deficiency "resistance."

One of skill will appreciate that soybean plant tolerance to low-available iron conditions varies widely, and can represent a spectrum of more-tolerant or less-tolerant phenotypes. However, by simple observation, one of skill can generally determine the relative tolerance or susceptibility of different plants, plant lines or plant families under low-available iron conditions, and furthermore, will also recognize the phenotypic gradations of "tolerant."

In one example, a plant's tolerance can be approximately quantitated using a chlorosis scoring system. In such a system, a plant that is grown in a known iron-deficient area, or in low-available iron experimental conditions, and is assigned a tolerance rating of between 1 (highly susceptible; most or all plants dead; those that live are stunted and have little living tissue) to 9 (highly tolerant; yield and survivability not significantly affected; all plants normal green color). See also, Dahiya and Singh (1979) "Effect of salinity, alkalinity and iron sources on availability of iron," Plant and Soil 51:13-18.

II. Description of the Invention: Overview

In accordance with the present invention, Applicants have discovered genomic regions, associated markers, and associated methods for identifying and associating genotypes that affect an iron deficient growth condition tolerance trait.

The advent of molecular genetic markers has facilitated mapping and selection of agriculturally important traits in soybean. Markers tightly linked to tolerance genes are an asset in the rapid identification of tolerant soybean lines on the basis of genotype by the use of marker assisted selection (MAS). Introgressing tolerance genes into a desired cultivar is also facilitated by using suitable nucleic acid markers.

The use of markers to infer a phenotype of interest results in the economization of a breeding program by substituting costly, time-intensive phenotyping assays with genotyping assays. Further, breeding programs can be designed to explicitly drive the frequency of specific, favorable phenotypes by targeting particular genotypes (U.S. Pat. No. 6,399,855). Fidelity of these associations may be monitored continuously to ensure maintained predictive ability and, thus, informed breeding decisions (U.S. Patent Application 2005/0015827). In this case, costly, time-intensive phenotyping assays required for determining if a plant or plants contains a genomic region associated with a low iron growth condition tolerant phenotype can be supplanted by genotypic assays that provide for identification of a plant or plants that contain the desired genomic region.

III. QTL Associated with Tolerance to Low Iron Growth Conditions

Provided herewith are certain other QTL that have also been identified as associated with a desirable phenotype of tolerance to growth in low iron conditions when present in certain allelic forms.

These several soybean QTL provided—that can be associated with a desirable low iron growth condition tolerant phenotype when present in certain allelic forms—are located on soybean chromosome 16 (soybean linkage group J), soybean chromosome 15 (soybean linkage group E), soybean chromosome 7 (soybean linkage group M), soybean chromosome 17 (soybean linkage group D2), and soybean chromosome 10 (soybean linkage group O).

Tables 1, 3, 5, 7, 9 (corresponding to chromosomes 16, 15, 7, 17, and 10, respectively) shows the relative positions of certain markers that have been disclosed in public databases and non-public (bolded) polymorphic nucleic acid markers, designated SEQ ID NOs, genetic positions (cM) on the chromosome, the allelic forms of certain polymorphic nucleic acid markers associated with a low iron growth condition tolerant phenotype, the allelic forms of those polymorphic nucleic acid markers not associated with the low iron growth condition tolerant phenotype, and the polymorphic position within the sequence of the polymorphic nucleic acid marker. The bolded markers have been identified as within a genomic region associated with a low iron growth condition tolerant phenotype.

Tables 2, 4, 6, 8, 10 (corresponding to chromosomes 16, 15, 7, 17, and 10, respectively) provides for each polymorphic nucleic acid marker/SEQ ID NO: the linkage group corresponding to the chromosome and the relative physical map positions of the markers.

TABLE 1

Chromosome 16—QTL on chromosome 16 associated with a low iron growth condition tolerant phenotype.

| Marker Locus Name/ SEQ ID NO. | cM Map Position on Chromosome Sixteen (16) | [-LOG10 (P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| asmbl_10470 | * | * | * | * | * |
| BI427060 | * | * | * | * | * |
| 1 | 104.6 | 3.2 | GG | AA | 201 |
| 2 | 104.9 | 3.9 | CC | GG | 201 |
| 3 | 105.2 | 2.9 | GG | AA | 201 |
| 4 | 105.5 | 3.9 | CC | AA | 281 |
| 5 | 105.6 | 3.2 | CC | TT | 618 |
| 6 | 105.6 | 2.8 | CC | AA | 201 |
| 7 | 105.7 | 3.0 | CC | TT | 201 |
| 8 | 106.2 | 2.9 | CC | TT | 201 |
| 9 | 106.3 | 3.1 | GG | CC | 201 |
| 10 | 106.4 | 3.8 | CC | TT | 201 |
| 11 | 107.1 | 3.6 | AA | CC | 201 |
| 12 | 107.2 | 3.2 | GG | CC | 201 |
| 13 | 107.3 | 2.7 | AA | GG | 201 |
| 14 | 107.6 | 3.6 | GG | AA | 201 |
| 15 | 107.6 | 2.5 | CC | TT | 176 |
| 16 | 107.9 | 2.5 | CC | TT | 201 |

TABLE 1-continued

Chromosome 16—QTL on chromosome 16 associated with a low iron growth condition tolerant phenotype.

| Marker Locus Name/ SEQ ID NO. | cM Map Position on Chromosome Sixteen (16) | [-LOG10 (P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| 17 | 108.5 | 2.7 | CC | TT | 201 |
| 18 | 108.8 | 3.3 | TT | CC | 201 |
| 19 | 108.8 | 2.6 | CC | TT | 201 |
| 20 | 108.8 | 3.0 | AA | CC | 925 |
| 21 | 109.5 | 2.2 | TT | CC | 201 |
| 22 | 109.8 | 2.4 | TT | AA | 380 |
| 23 | 110.1 | 2.5 | GG | AA | 201 |
| 24 | 110.5 | 4.0 | TT | AA | 201 |
| 25 | 110.8 | 4.3 | CC | AA | 639 |
| 26 | 113.8 | 3.3 | TT | AA | 123 |
| 27 | 111.1 | 5.0 | CC | TT | 201 |
| 28 | 111.3 | 2.5 | TT | CC | 201 |
| 29 | 111.4 | 2.4 | TT | CC | 201 |
| 30 | 111.5 | 2.8 | CC | AA | 201 |
| 31 | 111.7 | 3.7 | AA | GG | 201 |
| 32 | 112 | 2.8 | AA | GG | 201 |
| 33 | 112.1 | 2.6 | GG | CC | 201 |
| 34 | 112.3 | 4.4 | AA | GG | 201 |
| 35 | 112.6 | 3.3 | CC | AA | 201 |
| 36 | 112.8 | 3.1 | TT | CC | 347 |
| 37 | 112.9 | 2.9 | TT | CC | 201 |
| 38 | 113.1 | 2.8 | AA | GG | 201 |
| 39 | 113.4 | 2.9 | TT | GG | 201 |
| 40 | 113.6 | 2.6 | TT | CC | 201 |
| 41 | 113.7 | 2.7 | CC | TT | 201 |
| 42 | 113.7 | 2.8 | TT | CC | 155 |
| 43 | 113.7 | 3.0 | AA | GG | 261 |
| 44 | 113.8 | 2.4 | TT | CC | 201 |
| 45 | 113.8 | 2.3 | AA | GG | 194 |
| 46 | 113.9 | 2.7 | GG | TT | 201 |
| 47 | 114.1 | 2.4 | TT | CC | 201 |
| 48 | 114.4 | 2.4 | TT | CC | 285 |
| TA67482_3847 | * | * | * | * | * |
| TC370075 | * | * | * | * | * |

TABLE 2

Chromosome 16—Physical positions of certain genetic markers on soybean chromosome 16 in proximity to QTL associated with a low iron growth condition tolerant phenotype.

| Marker Locus Name/SEQ ID NO. | Linkage Group | Chromosome | Middle Position | Start Position | End Position |
|---|---|---|---|---|---|
| asmbl_10470 | J | 16 | 31363336 | 31362972 | 31363701 |
| BI427060 | J | 16 | 31363515 | 31363238 | 31363792 |
| 1 | J | 16 | 31369584 | 31369434 | 31369735 |
| 2 | J | 16 | 31443226 | 31443076 | 31443377 |
| 3 | J | 16 | 31477826 | 31478015 | 31477638 |
| 4 | J | 16 | 31480456 | 31480836 | 31480077 |
| 5 | J | 16 | 31486792 | 31486642 | 31486943 |
| 6 | J | 16 | 31480983 | 31480833 | 31481134 |
| 7 | J | 16 | 31510525 | 31510375 | 31510676 |
| 8 | J | 16 | 31516209 | 31516059 | 31516360 |
| 9 | J | 16 | 31521798 | 31521648 | 31521949 |
| 10 | J | 16 | 31553067 | 31552917 | 31553218 |
| 11 | J | 16 | 31557341 | 31557191 | 31557492 |
| 12 | J | 16 | 31563379 | 31563229 | 31563530 |
| 13 | J | 16 | 31574585 | 31574435 | 31574736 |
| 14 | J | 16 | 31575341 | 31575137 | 31575545 |
| 15 | J | 16 | 31577004 | 31576854 | 31577155 |
| 16 | J | 16 | 31580785 | 31580635 | 31580936 |
| 17 | J | 16 | 31614520 | 31614370 | 31614671 |

TABLE 2-continued

Chromosome 16—Physical positions of certain genetic markers on soybean chromosome 16 in proximity to QTL associated with a low iron growth condition tolerant phenotype.

| Marker Locus Name/SEQ ID NO. | Linkage Group | Chromosome | Middle Position | Start Position | End Position |
|---|---|---|---|---|---|
| 18 | J | 16 | 31614870 | 31615435 | 31614305 |
| 19 | J | 16 | 31618039 | 31617889 | 31618190 |
| 20 | J | 16 | 31643780 | 31643630 | 31643931 |
| 21 | J | 16 | 31785190 | 31785040 | 31785341 |
| 22 | J | 16 | 31804506 | 31804356 | 31804657 |
| 23 | J | 16 | 31831923 | 31831773 | 31832074 |
| 24 | J | 16 | 31889649 | 31889499 | 31889800 |
| 25 | J | 16 | 31904942 | 31904792 | 31905093 |
| 26 | J | 16 | 31911271 | 31911121 | 31911422 |
| 27 | J | 16 | 31925976 | 31925826 | 31926127 |
| 28 | J | 16 | 31952216 | 31952066 | 31952367 |
| 29 | J | 16 | 31990398 | 31990248 | 31990549 |
| 30 | J | 16 | 31997204 | 31997054 | 31997355 |
| 31 | J | 16 | 32031978 | 32031828 | 32032129 |
| 32 | J | 16 | 32079262 | 32079112 | 32079413 |
| 33 | J | 16 | 32100628 | 32100039 | 32101218 |
| 34 | J | 16 | 32154510 | 32154694 | 32154327 |
| 35 | J | 16 | 32161907 | 32161757 | 32162058 |
| 36 | J | 16 | 32204175 | 32204025 | 32204326 |
| 37 | J | 16 | 32242461 | 32242311 | 32242612 |
| 38 | J | 16 | 32279082 | 32278743 | 32279421 |
| 39 | J | 16 | 32291528 | 32291900 | 32291157 |
| 40 | J | 16 | 32347306 | 32347156 | 32347457 |
| 41 | J | 16 | 32434829 | 32446198 | 32423461 |
| 42 | J | 16 | 32484745 | 32484595 | 32484896 |
| 43 | J | 16 | 32519227 | 32519077 | 32519378 |
| 44 | J | 16 | 32672805 | 32672655 | 32672956 |
| 45 | J | 16 | 32852516 | 32852366 | 32852667 |
| 46 | J | 16 | 32852826 | 32852442 | 32853211 |
| 47 | J | 16 | 32854325 | 32854591 | 32854059 |
| 48 | J | 16 | 31374689 | 31374539 | 31374840 |
| TA67482_3847 | J | 16 | 32859166 | 32858544 | 32859789 |
| TC370075 | J | 16 | 32859832 | 32859787 | 32859877 |

TABLE 3

Chromosome 15—QTL on chromosome 15 associated with a low iron growth condition tolerant phenotype.

| Marker Locus Name/ SEQ ID NO | cM Map Position on Chromosome Fifteen (15) | [-LOG 10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| DB975811 | * | * | * | * | * |
| TA67841_3847 | * | * | * | * | * |
| 49 | 22.5 | 3.0 | TT | CC | 201 |
| 50 | 22.7 | 4.1 | CC | TT | 201 |
| 51 | 22.9 | 3.1 | CC | GG | 201 |
| 52 | 23.6 | 3.4 | TT | CC | 201 |
| 53 | 23.7 | 3.6 | CC | TT | 201 |
| 54 | 23.9 | 3.4 | TT | GG | 354 |
| 55 | 23.9 | 4.1 | CC | CC | 355 |
| 56 | 24.1 | 3.2 | TT | AA | 61 |
| 57 | 24.7 | 4.1 | AA | GG | 201 |
| 58 | 24.7 | 4.1 | GG | AA | 240 |
| 59 | 24.7 | 4.1 | GG | AA | 428 |
| 60 | 24.9 | 3.3 | CC | TT | 993 |
| 61 | 25.4 | 3.9 | TT | CC | 201 |
| 62 | 25.6 | 5.6 | TT | CC | 201 |
| 63 | 26.4 | 3.9 | CC | AA | 201 |
| 64 | 31.4 | 3.0 | TT | CC | 201 |
| 65 | 31.6 | 3.0 | TT | GG | 201 |
| 66 | 31.7 | 3.1 | AA | GG | 201 |
| 67 | 31.8 | 4.6 | GG | AA | 201 |
| 68 | 32.4 | 3.1 | AA | GG | 201 |
| 69 | 32.5 | 3.3 | GG | AA | 201 |
| TC370174 | * | * | * | * | * |
| Glyma15g06010 | * | * | * | * | * |

TABLE 4

Chromosome 15—Physical positions of certain genetic markers on soybean chromosome 5 in proximity to QTL associated with a low iron growth condition tolerant phenotype.

| Marker Locus Name/SEQ ID NO. | Linkage Group | Chromosome | Middle Position | Start Position | End Position |
|---|---|---|---|---|---|
| DB975811 | E | 15 | 2656905 | 2656345 | 2657466 |
| TA67841_3847 | E | 15 | 2656990 | 2656430 | 2657551 |
| 49 | E | 15 | 2657551 | 2657401 | 2657702 |
| 50 | E | 15 | 2674098 | 2673948 | 2674249 |
| 51 | E | 15 | 2701610 | 2701460 | 2701761 |
| 52 | E | 15 | 2796176 | 2796026 | 2796327 |
| 53 | E | 15 | 2822719 | 2822569 | 2822870 |
| 54 | E | 15 | 2847164 | 2847410 | 2846919 |
| 55 | E | 15 | 2847207 | 2847057 | 2847358 |
| 56 | E | 15 | 3039453 | 3039024 | 3039882 |
| 57 | E | 15 | 3043572 | 3043814 | 3043331 |
| 58 | E | 15 | 3048934 | 3048784 | 3049085 |
| 59 | E | 15 | 3154544 | 3154394 | 3154695 |
| 60 | E | 15 | 3178097 | 3177947 | 3178248 |
| 61 | E | 15 | 3301037 | 3300887 | 3301188 |
| 62 | E | 15 | 3402856 | 3402706 | 3403007 |
| 63 | E | 15 | 3756773 | 3756509 | 3757037 |
| 64 | E | 15 | 2662233 | 2662435 | 2662031 |
| 65 | E | 15 | 2663725 | 2663953 | 2663497 |
| 66 | E | 15 | 2667350 | 2667200 | 2667501 |
| 67 | E | 15 | 2697692 | 2697542 | 2697843 |
| 68 | E | 15 | 2722948 | 2722798 | 2723099 |
| 69 | E | 15 | 2729212 | 2729062 | 2729363 |
| TC370174 | E | 15 | 2772449 | 2772299 | 2772600 |
| Glyma15g06010 | E | 15 | 2790560 | 2790410 | 2790711 |

TABLE 5

Chromosome 7—QTL on chromosome 7 associated with a low iron growth condition tolerant phenotype.

| Marker Locus Name/ SEQ ID NO. | cM Map Position on Chromosome Seven (7) | [-LOG10 (P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| TA75172_3847 | * | * | * | * | * |
| Contig4349 | * | * | * | * | * |
| 70 | 46.7 | 1.5 | AA | GG | 201 |
| 71 | 51.8 | 1.5 | AA | GG | 650 |
| 72 | 53.5 | 1.9 | AA | TT | 201 |
| 73 | 53.7 | 2.0 | TT | GG | 201 |

TABLE 5-continued

Chromosome 7—QTL on chromosome 7 associated with a low iron growth condition tolerant phenotype.

| Marker Locus Name/ SEQ ID NO. | cM Map Position on Chromosome Seven (7) | [-LOG10 (P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| 74 | 54.5 | 1.8 | GG | TT | 201 |
| 75 | 58.6 | 1.4 | GG | AA | 201 |
| 76 | 58.9 | 1.5 | GG | AA | 201 |
| 77 | 59.6 | 1.4 | TT | CC | 201 |
| 78 | 59.7 | 2.4 | GG | AA | 201 |
| 79 | 59.8 | 2.1 | TT | CC | 201 |
| 80 | 96.4 | 3.0 | TT | CC | 201 |
| 81 | 98.2 | 3.0 | GG | CC | 201 |
| 82 | 98.6 | 3.2 | TT | CC | 201 |
| 83 | 102.1 | 2.3 | GG | AA | 201 |
| 84 | 102.8 | 2.2 | AA | GG | 201 |
| 85 | 102.9 | 2.2 | AA | GG | 201 |
| AW705305 | * | * | * | * | * |
| TC380682 | * | * | * | * | * |

TABLE 6

Chromosome 7—Physical positions of certain genetic markers on soybean chromosome 7 in proximity to QTL associated with a low iron growth condition tolerant phenotype.

| Marker Locus Name/ SEQ ID NO. | Linkage Group | Chromosome | Middle Position | Start Position | End Position |
|---|---|---|---|---|---|
| TA75172_3847 | M | 7 | 5421539 | 5421375 | 5421704 |
| Contig4349 | M | 7 | 5422610 | 5422460 | 5422761 |
| 70 | M | 7 | 6777792 | 6777642 | 6777943 |
| 71 | M | 7 | 6814309 | 6814159 | 6814460 |
| 72 | M | 7 | 6911064 | 6910914 | 6911215 |
| 73 | M | 7 | 7602143 | 7601993 | 7602294 |
| 74 | M | 7 | 7671547 | 7671397 | 7671698 |
| 75 | M | 7 | 7801323 | 7801173 | 7801474 |
| 76 | M | 7 | 7821649 | 7821499 | 7821800 |
| 77 | M | 7 | 7829639 | 7829489 | 7829790 |
| 78 | M | 7 | 17390045 | 17389895 | 17390196 |
| 79 | M | 7 | 17724916 | 17724766 | 17725067 |
| 80 | M | 7 | 17812664 | 17812514 | 17812815 |
| 81 | M | 7 | 18464522 | 18464372 | 18464673 |
| 82 | M | 7 | 18592542 | 18592392 | 18592693 |
| 83 | M | 7 | 18594332 | 18594182 | 18594483 |
| 84 | M | 7 | 18592542 | 18592392 | 18592693 |
| 85 | M | 7 | 18594332 | 18594182 | 18594483 |
| AW705305 | M | 7 | 18594647 | 18594463 | 18594831 |
| TC380682 | M | 7 | 18594649 | 18594451 | 18594848 |

TABLE 7

Chromosome 17—QTL on chromosome 17 associated with a low iron growth condition tolerant phenotype.

| Marker Locus Name/ SEQ ID NO | cM Map Position on Chromosome Seventeen (17) | [-LOG10 (P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| TC350035 | * | * | * | * | * |
| TA43074_3847 | * | * | * | * | * |
| 86 | 5.2 | 2.0 | GG | TT | 201 |
| 87 | 5.4 | 2.0 | TT | GG | 201 |
| 88 | 5.6 | 3.2 | CC | TT | 201 |
| 89 | 5.7 | 3.3 | AA | TT | 201 |
| 90 | 5.8 | 3.2 | TT | GG | 201 |
| 91 | 5.8 | 3.3 | AA | GG | 201 |
| 92 | 5.9 | 3.1 | GG | CC | 201 |
| 93 | 6 | 3.2 | TT | GG | 201 |
| 94 | 6.1 | 3.1 | GG | AA | 201 |
| 95 | 6.3 | 3.1 | AA | CC | 201 |
| 96 | 6.5 | 3.1 | AA | TT | 201 |
| 97 | 6.6 | 3.0 | TT | AA | 201 |
| 98 | 6.8 | 3.0 | GG | AA | 201 |
| 99 | 7.1 | 3.0 | GG | CC | 439 |
| 100 | 7.3 | 3.0 | CC | TT | 201 |
| 101 | 7.5 | 2.4 | CC | GG | 201 |
| 102 | 7.7 | 2.4 | CC | AA | 201 |
| 103 | 8 | 3.2 | AA | TT | 201 |
| 104 | 8.1 | 3.0 | GG | AA | 201 |
| 105 | 8.2 | 2.8 | TT | CC | 201 |
| 106 | 8.2 | 2.7 | GG | AA | 201 |
| 107 | 8.4 | 2.7 | TT | CC | 201 |
| 108 | 8.5 | 2.8 | CC | TT | 201 |
| 109 | 8.8 | 3.0 | TT | CC | 201 |
| 110 | 9 | 2.8 | AA | CC | 201 |
| 111 | 9.2 | 3.5 | TT | GG | 201 |
| 112 | 9.3 | 3.6 | TT | AA | 201 |
| Glyma17g01380 | * | * | * | * | * |
| Gm_W82_CR17.G8870 | * | * | * | * | * |

TABLE 8

Chromosome 17—Physical positions of certain genetic markers on soybean chromosome 17 in proximity to QTL associated with a low iron growth condition tolerant phenotype.

| Marker Locus Name/ SEQ ID NO | Linkage Group | Chromosome | Middle Position | Start Position | End Position |
|---|---|---|---|---|---|
| TC350035 | D2 | 17 | 280819 | 279005 | 282633 |
| TA43074_3847 | D2 | 17 | 280856 | 279080 | 282633 |
| 86 | D2 | 17 | 282695 | 282545 | 282846 |
| 87 | D2 | 17 | 317160 | 317010 | 317311 |
| 88 | D2 | 17 | 342956 | 342806 | 343107 |
| 89 | D2 | 17 | 349222 | 349072 | 349373 |
| 90 | D2 | 17 | 358930 | 358780 | 359081 |
| 91 | D2 | 17 | 368357 | 368207 | 368508 |
| 92 | D2 | 17 | 384568 | 384418 | 384719 |
| 93 | D2 | 17 | 397053 | 396903 | 397204 |
| 94 | D2 | 17 | 408927 | 408777 | 409078 |
| 95 | D2 | 17 | 435118 | 434968 | 435269 |
| 96 | D2 | 17 | 464163 | 464013 | 464314 |
| 97 | D2 | 17 | 479395 | 479245 | 479546 |
| 98 | D2 | 17 | 495991 | 495841 | 496142 |
| 99 | D2 | 17 | 545090 | 544843 | 545337 |
| 100 | D2 | 17 | 574773 | 574623 | 574924 |
| 101 | D2 | 17 | 602079 | 601929 | 602230 |
| 102 | D2 | 17 | 618344 | 618194 | 618495 |
| 103 | D2 | 17 | 670615 | 670465 | 670766 |
| 104 | D2 | 17 | 683816 | 683666 | 683967 |
| 105 | D2 | 17 | 685126 | 684976 | 685277 |
| 106 | D2 | 17 | 693456 | 693306 | 693607 |

TABLE 8-continued

Chromosome 17—Physical positions of certain genetic markers on soybean chromosome 17 in proximity to QTL associated with a low iron growth condition tolerant phenotype.

| Marker Locus Name/ SEQ ID NO | Linkage Group | Chromo- some | Middle Position | Start Position | End Position |
|---|---|---|---|---|---|
| 107 | D2 | 17 | 717263 | 717113 | 717414 |
| 108 | D2 | 17 | 732375 | 732225 | 732526 |
| 109 | D2 | 17 | 782062 | 781912 | 782213 |
| 110 | D2 | 17 | 809659 | 809509 | 809810 |
| 111 | D2 | 17 | 823632 | 823482 | 823783 |
| 112 | D2 | 17 | 840172 | 840022 | 840323 |
| Glyma17g01380 | D2 | 17 | 844200 | 842706 | 845694 |
| Gm_W82_CR17.G8870 | D2 | 17 | 844200 | 842706 | 845694 |

TABLE 9

Chromosome 10—QTL on chromosome 10 associated with a low iron growth condition tolerant phenotype.

| Marker Locus Name/SEQ ID NO | cM Map Position on Chromo- some Seven- teen (10) | [-LOG10 (P)] | Allelic Form(s) Asso- ciated With Low Fe Tolerance Pheno- type[1] | Allelic Form(s) Not-Asso- ciated with Low Fe Tolerance Pheno- type[1] | Poly- mor- phic Posi- tion |
|---|---|---|---|---|---|
| NA | * | * | * | * | * |
| WmFPC_Contig227 | * | * | * | * | * |
| 113 | 85.9 | 2.4 | TT | CC | 201 |
| 114 | 86.3 | 2.7 | CC | TT | 201 |
| 115 | 86.6 | 2.5 | AA | GG | 201 |
| 116 | 86.7 | 2.6 | CC | TT | 201 |
| 117 | 86.8 | 2.3 | CC | GG | 201 |
| 118 | 86.9 | 2.6 | GG | AA | 201 |
| 119 | 87.2 | 2.5 | CC | TT | 201 |
| 120 | 87.3 | 2.7 | TT | AA | 201 |
| 121 | 87.4 | 2.4 | GG | AA | 201 |
| 122 | 87.5 | 2.2 | CC | TT | 201 |
| 123 | 87.6 | 2.8 | CC | TT | 201 |
| 124 | 87.7 | 2.9 | CC | TT | 201 |
| 125 | 87.8 | 2.7 | GG | AA | 136 |
| 126 | 88 | 2.5 | TT | GG | 201 |
| 127 | 88.1 | 2.6 | CC | TT | 219 |
| 128 | 89.7 | 2.5 | AA | GG | 201 |
| 129 | 89.8 | 2.5 | GG | AA | 201 |
| 130 | 90.1 | 2.7 | AA | TT | 201 |
| 131 | 90.9 | 2.8 | TT | CC | 201 |
| 132 | 91.2 | 3.7 | AA | GG | 201 |
| 133 | 91.3 | 2.8 | AA | CC | 201 |
| 134 | 91.4 | 2.1 | GG | CC | 201 |
| 135 | 91.5 | 3.9 | AA | GG | 201 |
| 136 | 91.7 | 2.2 | TT | GG | 201 |
| 137 | 91.9 | 3.9 | TT | AA | 201 |
| 138 | 92 | 3.7 | GG | AA | 201 |
| 139 | 92.1 | 3.7 | CC | AA | 201 |
| 140 | 92.2 | 3.7 | GG | AA | 201 |
| 141 | 92.4 | 3.9 | TT | CC | 201 |
| 142 | 93.9 | 2.1 | GG | CC | 201 |
| 143 | 94.3 | 2.1 | GG | AA | 201 |
| 144 | 94.4 | 2.1 | TT | CC | 201 |
| 145 | 94.5 | 2.1 | CC | AA | 201 |
| 146 | 95.8 | 2.4 | TT | AA | 201 |
| 147 | 101 | 2.1 | CC | TT | 201 |
| Glyma10g28920 | * | * | * | * | * |
| Cf16144d | * | * | * | * | * |

TABLE 10

Chromosome 10—Physical positions of certain genetic markers on soybean chromosome 10 in proximity to QTL associated with a low iron growth condition tolerant phenotype.

| Marker Locus Name/ SEQ ID NO | Link- age Group | Chromo- some | Middle Position | Start Position | End Position |
|---|---|---|---|---|---|
| NA | O | 10 | 29358961 | 11677282 | 47040641 |
| WmFPC_Contig227 | O | 10 | 29398139 | 28618646 | 30177632 |
| 113 | O | 10 | 29720865 | 29720715 | 29721016 |
| 114 | O | 10 | 30158032 | 30157882 | 30158183 |
| 115 | O | 10 | 30164795 | 30164645 | 30164946 |
| 116 | O | 10 | 30168646 | 30168496 | 30168797 |
| 117 | O | 10 | 30173472 | 30173322 | 30173623 |
| 118 | O | 10 | 30197793 | 30197643 | 30197944 |
| 119 | O | 10 | 30250601 | 30250451 | 30250752 |
| 120 | O | 10 | 30265182 | 30265032 | 30265333 |
| 121 | O | 10 | 30296454 | 30296304 | 30296605 |
| 122 | O | 10 | 30302927 | 30302777 | 30303078 |
| 123 | O | 10 | 30338781 | 30338631 | 30338932 |
| 124 | O | 10 | 30339883 | 30339733 | 30340034 |
| 125 | O | 10 | 30368472 | 30368234 | 30368710 |
| 126 | O | 10 | 30785142 | 30784992 | 30785293 |
| 127 | O | 10 | 30923459 | 30923014 | 30923904 |
| 128 | O | 10 | 36092106 | 36091956 | 36092257 |
| 129 | O | 10 | 36297861 | 36297711 | 36298012 |
| 130 | O | 10 | 37237431 | 37237281 | 37237582 |
| 131 | O | 10 | 37349903 | 37349753 | 37350054 |
| 132 | O | 10 | 37364859 | 37364709 | 37365010 |
| 133 | O | 10 | 37381677 | 37381527 | 37381828 |
| 134 | O | 10 | 37396158 | 37396008 | 37396309 |
| 135 | O | 10 | 37396896 | 37396746 | 37397047 |
| 136 | O | 10 | 37428843 | 37428693 | 37428994 |
| 137 | O | 10 | 37453860 | 37453710 | 37454011 |
| 138 | O | 10 | 37465158 | 37465008 | 37465309 |
| 139 | O | 10 | 37479303 | 37479153 | 37479454 |
| 140 | O | 10 | 37492059 | 37491909 | 37492210 |
| 141 | O | 10 | 37525000 | 37524850 | 37525151 |
| 142 | O | 10 | 37718944 | 37718794 | 37719095 |
| 143 | O | 10 | 37753981 | 37753831 | 37754132 |
| 144 | O | 10 | 37761477 | 37761327 | 37761628 |
| 145 | O | 10 | 37763485 | 37763284 | 37763687 |
| 146 | O | 10 | 37898074 | 37897924 | 37898225 |
| 147 | O | 10 | 38394420 | 38394270 | 38394571 |
| Glyma10g28920 | O | 10 | 38395822 | 38395602 | 38396043 |
| Cf16144d | O | 10 | 38397079 | 38396831 | 38397328 |

IV. Identification of Plants Exhibiting Tolerance to Low Iron Growth Conditions

To observe the presence or absence of low iron growth condition tolerant phenotypes, soybean plants comprising genotypes of interest can be exposed to low iron or iron deficient growth conditions in seedling stages, early to mid-vegetative growth stages, or in early reproductive stages. Experienced plant breeders can recognize tolerant soybean plants in the field, and can select the tolerant individuals or populations for breeding purposes or for propagation. In this context, the plant breeder recognizes "tolerant" and "susceptible" soybean plants in fortuitous naturally-occurring filed observations.

Breeders will appreciate that plant tolerance is a phenotypic spectrum consisting of extremes in tolerance, susceptibility, and a continuum of intermediate phenotypes. Tolerance also varies due to environmental effects. Evaluation of phenotypes using reproducible assays and tolerance scoring methods are of value to scientists who seek to identify genetic loci that impart tolerance, conduct marker assisted selection to create tolerant soybean populations, and for introgression techniques to breed a tolerance trait into an elite soybean line, for example.

In contrast to fortuitous field observations that classify plants as either "tolerant" or "susceptible," various methods are known in the art for determining (and quantitating) the tolerance of a soybean plant to iron-deficient growth conditions. These techniques can be applied to different fields at different times, or to experimental greenhouse or laboratory settings, and provide approximate tolerance scores that can be used to characterize the tolerance of a given strain or line regardless of growth conditions or location. See, for example, Diers et al. (1992) "Possible identification of quantitative trait loci affecting iron efficiency in soybean," J. Plant Nutr. 15:217-2136; Dahiya and M. Singh (1979) "Effect of salinity, alkalinity and iron sources on availability of iron," Plant and Soil 51:13-18; and Gonzalez-Vallejo et al. (2000) "Iron Deficiency Decreases the Fe(III)-Chelate Reducing Activity of Leaf Protoplasts" Plant Physiol. 122 (2): 337-344.

The degree of IDC in a particular plant or stand of plants can be quantitated by using a system to score the severity of the disease in each plant. A plant strain or variety or a number of plant strains or varieties are planted and grown in a single stand in soil that is known to produce chlorotic plants as a result of iron deficiency ("field screens," i.e., in fields that have previously demonstrated IDC), or alternatively, in controlled nursery hydroponic conditions. When the assay is conducted in controlled nursery conditions, defined soils can be used, where the concentration of iron (e.g., available iron) has been previously measured. The plants can be scored at maturity, or at any time before maturity.

Fifteen (15) to twenty (20) soybean plants are planted and grown in a greenhouse. After a ten (10) day period, the plants are moved to a growth chamber. The growth chamber is kept at 25° C. day, 22° C. night with a relative humidity of 60% and light intensity of 200-500 microeinsteins and under a 16 hr photo-period. Water (3.5 gallons) plus the IDC nutrient solution is added to each test box. Water (3.5 gallons) plus the IDC nutrient solution and iron is added to the control box. Once boxes are filled with water and the solution, the pH is measured and adjusted to a range of 7.8-8.0. Nine (9) of the 15-20 plants are selected from each line. Two 3-plant groupings will be placed in two different boxes and the third grouping will be placed in the control box. Plants are kept in the growth chamber for a period of five (5) days. During that time, pH is measured and adjusted as necessary. At day five (5), all three (3) plants are evaluated as a group with a phenotypic score of 1-5. Plants receive a score of 1 if their leaves remain green, show no yellowing, and are comparable to the control within the control box. Additional scores will be given from a range of 1 (no yellowing) to 5 (severe yellowing) compared to their internal check lines. Nursey hydroponic conditions are normalized (1-9 scale) to correspond with disease ratings of soybean plants in field conditions.

The scoring system rates each plant on a scale of one (1) (most tolerant-no disease) to nine (9) (most susceptible-most severe disease), as shown in Table 11.

TABLE 11

IDC Score Ratings

| Plant or Plant Stand Score | Symptoms |
|---|---|
| 9 | Most plants are completely dead. The plants that are still alive are approximately 10% of normal height, and have very little living tissue. |
| 8 | Most leaves are almost dead, most stems are still green. Plants are severely stunted (10-20% of normal height). |

TABLE 11-continued

IDC Score Ratings

| Plant or Plant Stand Score | Symptoms |
|---|---|
| 7 | Most plants are yellow and necrosis is seen on most leaves. Most plants are approximately 20-40% of normal height. |
| 6 | Most plants are yellow, and necrosis is seen on the edges of less than half the leaves. Most plants are approximately 50% of normal height. |
| 5 | Most plants are light green to yellow, and no necrosis is seen on the leaves. Most plants are stunted (50-75% of normal height). |
| 4 | More than half the plants show moderate chlorosis, but no necrosis is seen on the leaves. |
| 3 | Less than half of the plants showing moderate chlorosis (light green leaves). |
| 2 | A few plants are showing very light chlorosis on one or two leaves. |
| 1 | All plants are normal green color. |

It will be appreciated that any such scale is relative, and furthermore, there may be variability between practitioners as to how the individual plants and the entire stand as a whole are scored. Optionally, the degree of chlorosis can be measured using a chlorophyll meter, e.g., a Minolta SPAD-502 Chlorophyll Meter, where readings off a single plant or a stand of plants can be made. Optionally, multiple readings can be obtained and averaged.

In general, while there is a certain amount of subjectivity to assigning severity measurements for disease symptoms, assignment to a given scale as noted above is well within the ordinary skill of a practitioner in the field. Measurements can also be averaged across multiple scores to reduce variation in field measurements.

V. Introgression of a Genomic Region Associated with a Low Iron Growth Condition Tolerance Phenotype Provided herewith are unique soybean germplasms comprising one or more introgressed genomic regions, QTL, or polymorphic nucleic acid markers associated with a low iron growth condition tolerant phenotype and methods of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic locus from a first germplasm (e.g., a low iron growth condition tolerant germplasm) and both linked and unlinked markers characteristic of the desired genetic background of a second germplasm (e.g., a low iron growth condition susceptible germplasm). In addition to the polymorphic nucleic acid markers provided herewith that identify alleles of certain QTL associated with a low iron growth condition tolerant phenotype, flanking markers that fall on both the telomere proximal end and the centromere proximal end of the genomic intervals comprising the QTL are also provided in Tables 1-10. Such flanking markers are useful in a variety of breeding efforts that include, but are not limited to, introgression of genomic regions associated with a low iron growth condition tolerant phenotype into a genetic background comprising markers associated with germplasm that ordinarily contains a genotype associated with a susceptible phenotype and maintenance of those genomic regions associated with a low iron growth condition tolerant phenotype in a plant population. Numerous markers that are linked and either immediately adjacent or adjacent to a low iron growth condition tolerant QTL in soybean that permit introgression of low iron growth condition tolerant QTL in the absence of extraneous linked DNA from the source germplasm containing the QTL are provided herewith. In certain embodiments, the linked and immediately adjacent markers are within about 105 kilobases (kB), 80 kB, 60 kB, 50 kB, 40 kB, 30 kB, 20 kB, 10 kB, 5 kB, 1 kB, 0.5 kB, 0.2 kB, or 0.1 kB of the introgressed genomic region. In certain embodiments, the linked and adjacent markers are within 1,000 kB, 600 kB, 500 kB, 400 kB, 300 kB, 200 kB, or 150 kB of the introgressed genomic region. In certain embodiments, the linked markers are genetically linked within about 50 cM, 40 cM, 30 cM, 20 cM, 10 cM, 5 cM, 4 cM, 3 cM, 2 cM, or 1 cM of the introgressed genomic region. In certain embodiments, genomic regions comprising some or all of one or more of a low iron growth condition tolerant QTL described herein can be introgressed into the genomes of susceptible varieties by using markers that include, but are not limited to, genetically linked markers, adjacent markers, and/or immediately adjacent markers provided in Tables 1-10. Those skilled in the art will appreciate that when seeking to introgress a smaller genomic region comprising a low iron growth condition tolerant QTL locus described herein, that any of the telomere proximal or centromere proximal markers that are genetically linked to or immediately adjacent to a larger genomic region comprising a low iron growth condition tolerant QTL locus can also be used to introgress that smaller genomic region.

Provided herein are methods of introgressing any of the genomic regions comprising a low iron growth condition tolerance QTL locus of Tables 1-10 into soybean germplasm that lacks such a locus. In certain embodiments, the soybean germplasm that lacks such a genomic region comprising a low iron growth condition tolerance QTL locus of Tables 1-10 is susceptible or has less than optimal levels of tolerance to low iron growth conditions. In certain embodiments, the methods of introgression provided herein can yield soybean plants comprising introgressed genomic regions comprising one or more low iron growth condition tolerance QTL loci of Tables 1-10, where the immediately adjacent genomic DNA and/or some or all of the adjacent genomic DNA between the introgressed genomic region and the telomere or centromere will comprise allelic forms of the markers of Tables 1-11 that are characteristic of the germplasm into which the genomic region is introgressed and distinct from the germplasm from which the genomic region is derived. In certain embodiments, the soybean germplasm into which the genomic region is introgressed is germplasm that lacks such a low iron growth condition tolerance locus. In certain embodiments, the soybean germplasm into which the genomic region is introgressed is germplasm that lacks such a low iron growth condition tolerance locus and is either susceptible to low iron growth conditions or has less than optimal tolerance to low iron growth conditions.

Also provided herein are soybean plants produced by the aforementioned methods of introgression. In certain embodiments, the soybean plants will comprise introgressed genomic regions comprising a low iron growth condition tolerance QTL locus of Tables 1-10, where the immediately adjacent genomic DNA and/or some or all of the adjacent genomic DNA between the introgressed genomic region and the telomere or centromere will comprise allelic forms of the markers of Tables 1-10 that are characteristic of the germplasm into which the genomic region is introgressed and distinct from the germplasm from which the genomic region is derived.

Soybean plants or germplasm comprising an introgressed genomic region that is associated with a low iron growth condition tolerant phenotype, wherein at least 10%, 25%, 50%, 75%, 90%, or 99% of the remaining genomic sequences carry markers characteristic of soybean plants or germplasm that are otherwise or ordinarily comprise a genomic region associated with susceptibility to low iron growth conditions, are thus provided. Furthermore soybean plants comprising an introgressed region where closely linked regions adjacent and/or immediately adjacent to the genomic regions, QTL, and markers provided herewith that comprise genomic sequences carrying markers characteristic of soybean plants or germplasm that are otherwise or ordinarily comprise a genomic region associated with the susceptibility to low iron growth conditions are also provided.

Also provided herein are methods of creating a population of soybean plants with enhanced tolerance to low iron growth conditions. In certain embodiments, the maintenance of a low iron growth condition tolerance QTL locus is achieved by providing a population of soybean plants, detecting the presence of a genetic marker that is genetically linked to the QTL, selecting one or more soybean plants containing said marker from the first population of soybean plants, and producing a population of offspring from the at least one selected soybean plants. In certain embodiments, the tolerance QTL are selected from Tables 1-10. In certain embodiments, the markers are genetically linked to the QTL in Tables 1-10. In certain embodiments, the markers are genetically linked to the tolerance QTL within 20 cM, 15 cM, 10 cM, 5 cM, 4 cM, or 3 cM. In certain embodiments, the genetic markers are selected from SEQ ID NOs. 1-147.

VI. Soybean Donor Plants Comprising Genomic Region Associated with Low Iron Growth Condition Phenotypes Low iron growth condition tolerance QTL allele or alleles can be introduced from any plant that contains that allele (donor) to any recipient soybean plant. In one aspect, the recipient soybean plant can contain additional low iron growth condition tolerance loci. In another aspect, the recipient soybean plant can contain a transgene. In another aspect, while maintaining the introduced QTL, the genetic contribution of the plant providing the low iron growth condition tolerance QTL can be reduced by back-crossing or other suitable approaches. In one aspect, the nuclear genetic material derived from the donor material in the soybean plant can be less than or about 50%, less than or about 25%, less than or about 13%, less than or about 5%, 3%, 2% or 1%, but that genetic material contains the low iron growth condition tolerance locus or loci of interest.

Plants containing one or more of the low iron growth condition tolerance loci described herein can be donor plants. In certain embodiments, a donor plant can be a susceptible line. In certain embodiments, a donor plant can also be a recipient soybean plant. A non-limiting and exemplary list of soybean varieties that are believed to comprise genomic regions associated with a low iron growth condition tolerance phenotype include, but are not limited to AG00501, AG00901, AG0131, AG0202, AG0231, AG0331, AG0401, AG801, AG0808, AG1031, AG1102, AG1230, AG2131, DKB22-52, AG3039, and AG3830 (Branded names of ASGROW (designated "AG") and DEKALB soybean varieties from Monsanto CO., 800 N. Lindbergh Blvd., St. Louis, Mo., USA.)

In a preferred embodiment, the soybean plants that comprise a genomic region associated with a low iron growth condition tolerance phenotype that are identified by use of the markers provided in Tables 1-10 and/or methods provided herein are soybean pre-commercial lines evaluated in an association study using a linear model and which is adjusted for stratification by principle components in the R GenABEL package.

In certain embodiment, a donor soybean plant is AG801 and derivatives thereof, and is used as the resistant parent in a bi-parental mapping population to select for genomic regions associated with a low iron growth condition tolerance phenotype.

Also provided herewith are additional soybean plants that comprise a genomic region associated with a low iron growth condition tolerance phenotype that are identified by use of the markers provided in Tables 1-11 and/or methods provided herein. Any of the soybean plants identified above or other soybean plants that are otherwise identified using the markers or methods provided herein can be used in methods that include, but are not limited to, methods of obtaining soybean plants with an introgressed low iron growth condition tolerance locus, obtaining a soybean plant that exhibits a low iron growth condition tolerance phenotype, or obtaining a soybean plant comprising in its genome a genetic region associated with a low iron growth condition tolerance phenotype.

In certain embodiments, the soybean plants provided herein or used in the methods provided herein can comprise a transgene that confers tolerance to glyphosate. Transgenes that can confer tolerance to glyphosate include, but are not limited to, transgenes that encode glyphosate tolerant Class I EPSPS (5-enolpyruvylshikimate-3-phosphate synthases) enzymes or glyphosate tolerant Class II EPSPS (5-enolpyruvylshikimate-3-phosphate synthases) enzymes. Useful glyphosate tolerant EPSPS enzymes provided herein are disclosed in U.S. Pat. No. 6,803,501, RE39,247, U.S. Pat. Nos. 6,225,114, 5,188,642, and 4,971,908. In certain embodiments, the glyphosate tolerant soybean plants can comprise a transgene encoding a glyphosate oxidoreductase or other enzyme which degrades glyphosate. Glyphosate oxidoreductase enzymes had been described in U.S. Pat. No. 5,776,760 and U.S. Reissue Pat. No. RE38,825. In certain embodiments the soybean plant can comprise a transgene encoding a glyphosate N-acetyltransferase gene that confers tolerance to glyphosate. In certain embodiments, the soybean plant can comprise a glyphosate n-acetyltransferase encoding transgene such as those described in U.S. Pat. No. 7,666,644. In still other embodiments, soybean plants comprising combinations of transgenes that confer glyphosate tolerance are provided. Soybean plants comprising both a glyphosate resistant EPSPS and a glyphosate N-acetyltransferase are also provided herewith. In certain embodiments, it is contemplated that the soybean plants used herein can comprise one or more specific genomic insertion(s) of a glyphosate tolerant transgene including, but not limited to, as those found in: i) MON89788 soybean (deposited under ATCC accession number PTA-6708 and described in US Patent Application Publication Number 20100099859), ii) GTS 40-3-2 soybean (Padgette et al., Crop Sci. 35: 1451-1461, 1995), iii) event 3560.4.3.5 soybean (seed deposited under ATCC accession number PTA-8287 and described in U.S. Patent Publication 20090036308), or any combination of i (MON89788 soybean), ii (GTS 40-3-2 soybean), and iii (event 3560.4.3.5 soybean).

A low iron growth condition tolerance associated QTL of the present invention may also be introduced into a soybean line comprising one or more transgenes that confer tolerance to herbicides including, but not limited to, glufosinate, dicamba, chlorsulfuron, and the like, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. These agronomic traits can be provided by the methods of plant biotechnology as transgenes in soybean.

In certain embodiments, it is contemplated that genotypic assays that provide for non-destructive identification of the plant or plants can be performed either in seed, the emergence stage, the "VC" stage (i.e. cotyledons unfolded), the V1 stage (appearance of first node and unifoliate leaves), the V2 stage (appearance of the first trifoliate leaf), and thereafter. In certain embodiments, non-destructive genotypic assays are performed in seed using apparati and associated methods as described in U.S. Pat. Nos. 6,959,617; 7,134,351; 7,454,989; 7,502,113; 7,591,101; 7,611,842; and 7,685,768, which are incorporated herein by reference in their entireties. In certain embodiments, non-destructive genotypic assays are performed in seed using apparati and associated methods as described in U.S. Patent Application Publications 20100086963, 20090215060, and 20090025288, which are incorporated herein by reference in their entireties. Published U.S. Patent Applications US 2006/0042527, US 2006/0046244, US 2006/0046264, US 2006/0048247, US 2006/0048248, US 2007/0204366, and US 2007/0207485, which are incorporated herein by reference in their entirety, also disclose apparatus and systems for the automated sampling of seeds as well as methods of sampling, testing and bulking seeds. Thus, in certain embodiments, any of the methods provided herein can comprise screening for markers in individual seeds of a population wherein only seed with at least one genotype of interest is advanced.

VII. Molecular Assisted Breeding Techniques

Genetic markers that can be used in the practice of the instant invention include, but are not limited to, are Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (U.S. Patent Applications 2005/0204780, 2005/0216545, 2005/0218305, and 2006/00504538). The resulting "genetic map" is the representation of the relative position of characterized loci (DNA markers or any other locus for which alleles can be identified) along the chromosomes. The measure of distance on this map is relative to the frequency of crossover events between sister chromatids at meiosis.

As a set, polymorphic markers serve as a useful tool for fingerprinting plants to inform the degree of identity of lines or varieties (U.S. Pat. No. 6,207,367). These markers can form a basis for determining associations with phenotype and can be used to drive genetic gain. The implementation of marker-assisted selection is dependent on the ability to detect underlying genetic differences between individuals.

Certain genetic markers for use in the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers that include. but are not limited, to single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al. 2003 Gen. Res. 13:513-523), microarray transcription profiles, DNA-derived sequences, and RNA-derived sequences that are genetically linked to or correlated with low iron growth condition tolerance loci, regions flanking low iron growth condition tolerance loci, regions linked to low iron growth condition tolerance loci, and/or regions that are unlinked to low iron growth condition tolerance loci can be used in certain embodiments of the instant invention.

In one embodiment, nucleic acid-based analyses for determining the presence or absence of the genetic polymorphism (i.e. for genotyping) can be used for the selection of seeds in a breeding population. A wide variety of genetic markers for the analysis of genetic polymorphisms are available and known to those of skill in the art. The analysis may be used to select for genes, portions of genes, QTL, alleles, or genomic regions (Genotypes) that comprise or are linked to a genetic marker that is linked to or correlated with low iron growth condition tolerance loci, regions flanking low iron growth condition tolerance loci, regions linked to low iron growth condition tolerance loci, and/or regions that are unlinked to low iron growth condition tolerance loci can be used in certain embodiments of the instant invention.

Herein, nucleic acid analysis methods include, but are not limited to, PCR-based detection methods (for example, TaqMan assays), microarray methods, mass spectrometry-based methods and/or nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201, 184; U.S. Pat. Nos. 4,683,202; 4,582,788; and 4,683,194), using primer pairs that are capable of hybridizing to the proximal sequences that define a polymorphism in its double-stranded form.

Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800, 944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005)). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616, 464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R.F. Service Science (2006) 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs, particularly in the case of genotypes.

What is claimed is:

1. A method of creating a population of soybean plants with a low iron growth condition tolerant phenotype, said method comprising:
   a. genotyping a first population of soybean plants or seeds;
   b. detecting in said first population of soybean plants or seeds, a polymorphic nucleic acid marker linked by less than or equal to 10 cM to an allele of SEQ ID NO:70, wherein said allele of SEQ ID NO:70 is associated with a low iron growth condition tolerant phenotype;
   c. selecting based upon said genotyping a soybean plant or seed containing said allele that was detected by genotyping;
   d. crossing or selfing said selected soybean plant or a plant produced from said selected seed; and
   e. producing from said crossing or selfing a population of progeny plants comprising said allele of SEQ ID NO:70 that is associated with the low iron growth condition tolerant phenotype;
   wherein said allele of SEQ ID NO:70 comprises an Adenosine at position 201.

2. A method of claim 1, wherein said marker locus is genetically linked by less than or equal to 5 cM to SEQ ID NO:70.

3. The method of claim 1, wherein said marker locus is in a genomic region flanked by SEQ ID NO:70 and SEQ ID NO:74.

4. The method of claim 1, wherein said marker locus is genetically linked by less than or equal to 1 cM to SEQ ID NO:70.

5. The method of claim 1, wherein said marker locus is from a chromosome region flanked by any two of marker loci selected from the group consisting of SEQ ID NOs: 70 to 74.

6. The method of claim 1, wherein said marker locus is of a marker type selected from the group consisting of Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD).

7. The method of claim 1, wherein said detecting an allele comprising a method selected form the group consisting of a PCR-based detection method, a microarray method, and a nucleic acid sequencing method.

8. The method of claim 1, wherein said detecting an allele comprising a single base extension (SBE) assay.

* * * * *

SEQUENCE LISTING

```
<160> NUMBER OF SEQ ID NOS: 147

<210> SEQ ID NO 1
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 1
ttgctttcat ttgttacaaa gcaacaattc tctctttagt acatgttgag caaagtgaat      60
caggcaactt atcaaagtag tcccatgttg catgataaag aagaggaaaa tagaaagaat     120
tttcagttaa ccgaaaaagt acaatgtncc ntttagataa attgaaaatg aaacaatatg     180
ttatcatgnt tctatcctcc aattcataca tgaccttttt gctttacgtg aaggaggacc     240
tcatccaatt gttggataat caaaatgaga aaagtcctca tctnaatgat tatttctctc     300
g                                                                     301

<210> SEQ ID NO 2
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 2
ttaacctnct atatgtatct cagtctcttc cttttctttc atttgctcat aattagaact      60
ataaaatagg cttaacccga caaactgacc cattagcctg ttagggcggg tcaagctggg     120
cccaagaaaa ttcggcctga atagaacttg gtcaatctgg gtactctgat aggcccagac     180
```

```
cgagctcaag aattacaaat ccaagttcaa tcaggnctat tatagtccaa cattattttt      240 atttttatc ctttaaattt atataaatcc agacaaaatt ttaaaacggg ccattgggct      300
a                                                                     301
```

<210> SEQ ID NO 3
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 3

```
gtatacagaa acagacaata atctcttact taattttcca ctagtcattg tttaacccaa       60
tgctggaaag tgatctttct aaagactcat tttatcatat tgaaaagtag ctttgaccga      120
ataaagcatt gtacattctt ttttgtgctt tgcggtaggt tccattggaa tgcacttcga      180
tatgtttaca tctaaatcca attttgggtc atacattcat tattatgttt ctaagccata      240
aatataagat aagtgttgca tatatttaag tttattggat tgcacttcgt attatntata      300
t                                                                     301
```

<210> SEQ ID NO 4
<211> LENGTH: 378
<212> TYPE: DNA
<213> ORGANISM: Glycine max

<400> SEQUENCE: 4

```
agatctaaca aggtaatttt tcccttaact atttgaaact cattatcaca acttggtaaa       60
agttaccttt caattgtcaa atttaaaacc catcacataa aatgccacaa atacatgcca      120
caccaaaatt tgcaagagaa ttcaaccaca ctgcagatct gcttcaggta gcagttcatc      180
gtgatacttt caccatactc aagcagaaag gtatatacaa agtactcatt tttttttgtt      240
aagaatgtga gggtaaagac caatttctga cccaatctgt aagagttgcc acatttctac      300
taacgtcttc tatattatca ctcttcattg caatcacttt ctcctccgag taactttctt      360
tagcctcctc aagcaaaa                                                   378
```

<210> SEQ ID NO 5
<211> LENGTH: 760
<212> TYPE: DNA
<213> ORGANISM: Glycine max

<400> SEQUENCE: 5

```
gccttgggtt cttgatgttg ccaagaaatt tgggctactt ggtgctactt tcttcactca       60
gacatgcaca acaaacaaca tatacttcca tgtttataag aagttgatag agttgcctct      120
tacacaggca gaatatttgt tgccagggtt gccaaaactt gcagctgggg acttgccatc      180
tttcttgaac aaatatgggt cctatccagg ctactttgat gtagttgtga atcaatttgt      240
caacattgat aaagcagatt gggttcttgc aaacagtttt tatgaactgg agcaaggggt      300
aagtgacttg actagctgaa aattctcttc attaatttga tttgtactta tttgttggaa      360
tgaattagac agcagtagtt atctgggtaa aaagttttc cttcaaattt tggtcaaaat      420
ttgtcctagt tcctattact tcaggatgat tctggtcttc ttttttattt ataattgatg      480
gattttgtct ctcatcctag tatcctaagt tccataaaaa gagaaaaat tcatcaatta      540
```

```
taaaaagaat tcaaagacca aaaatatcat ttttaaagta taacgactaa gaacaatttt      600
gattgaaatt agagagatct agaatacatt tttatcctag ttattttgtt ggataatatt      660
gatgattgaa atttgaaatg aaatttattg taggttgtgg attggctggt gaagatttgg      720
ccattaaagc aataggacc atgcctgcca tctatctact                             760
```

```
<210> SEQ ID NO 6
<211> LENGTH: 301
<212> TYPE: DNA
<213> ORGANISM: Glycine max

<400> SEQUENCE: 6
taggacccat atttgttcaa gaaagatggc aagtccccag ctgcaagttt tgcaaccct        60 ggcaacaaat attctgcctg tgtaagaggc aactctatca acttcttata aacatggaag      120
tatatgttgt ttgttgtgca tgtctgagtg aagaaagtag caccaagtag cccaaatttc      180
ttggcaacat caagaaccca aggcatgaaa gcatcataga taacacaatc tggagggtgg      240
cttgaccctg caagcttctg aacaagctca gcaaaagttt gtgatccaac cctccaaaag      300
g                                                                      301
```

```
<210> SEQ ID NO 7
<211> LENGTH: 301
<212> TYPE: DNA
<213> ORGANISM: Glycine max

<400> SEQUENCE: 7
agaacagaac aattcattta tgcggttatt gtttggtttt gcaggttaga gctgcagagc       60
tgaggaagat attggtggag cttgggccgg tatgtaatgc tggattgaat gcataataat      120
tcagttttag tagtggtttt tcttaattgc tattttcttt taattggttg atttggttca      180
ttgctgtttt atactacttt tttgcaggca tatatcaaaa ttgcccaggc tatatcatcc      240
cgtgctgtaa gttttggttt atctgtcaca ttattaaaac tgatctccat gttctttggt      300
t                                                                      301
```

```
<210> SEQ ID NO 8
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 8
tatcctttgc gatggtttgg gcatgaatac ttgatactta cctagagaaa aggttaaatt       60
taatatcatc atgatcttct tcctaaatga tgttgtgtgc cttttgagtt tcgagattta      120
gttcttggat atatgcctga agtgtttctc ccttgaaaac aagttaaggc atataggaa       180 aatttgtctt tacacattct tgtttgttgc ttgctgaaaa aagttgagaa ttctgctgat      240
gcactatggt atggctattg tagggggnaa agttgtctga agtgaaggat ctctacctga      300
t                                                                      301
```

```
<210> SEQ ID NO 9
<211> LENGTH: 301
<212> TYPE: DNA
<213> ORGANISM: Glycine max
<220> FEATURE:
<221> NAME/KEY: unsure
```

<222> LOCATION: (1)..(301)
<223> OTHER INFORMATION: unsure at all n locations

<400> SEQUENCE: 9

```
ttttcttgtt ggntcgtaaa ttgcaatatg gggatctttt ttggatttta cttgttttat      60
tatacctgac ttttagtcaa tcgttcagca ataggtatat taaacttgga acgctanatg     120
gacaatcatt ttactgtttt gtttatccta ataaaaaaaa ttgtactttt catcaatgac     180
atgtaggaaa gcanacaggc cagtcctgac aagaatcaaa tactgtacat ggaggagttg     240
tcgttagttt taaatcaagt tgaatccatt caagacattc ttcctataat ttctgtcatt     300
c                                                                     301
```

<210> SEQ ID NO 10
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 10

```
aatgaaccaa tttgaaggaa acaaacaaat taaagctgta aaaatnaana atatccaatt      60
attacccgt gttcttttag aaattgaatg gaatcatgtg tactgcacta taaatgacca     120
ccaaataaat ggtttattta acaaagtgga atccatgtct tcaaacaagt agcacgaagg     180
acatcaaaac catagttcac tgaaggacgc tagtttaaat ttcatcnttt tagtgaactt     240
caatgtaatt aaataaatca aaggatggga tatacatgtt gtttgaagac tcattggacg     300
g                                                                     301
```

<210> SEQ ID NO 11
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 11

```
tttcttggtt gaaatttccg caacctcctc ctttgtaatt tccttgacct ttacctctat      60
aatttcctct tcctccattg ttgagattat nacaaacttt gctttgtgca ctttgacttg     120
attcaacaac acttttgaga ttcacctgac tcttttaaggc ttcttcagtt acttttttcaa     180
tcttcttcaa gattctactc atgtgacttt ttgatgcttc cctgcaaata tgctattgtc     240
gtggtgtaga atgggatggt gttaggattt tgtccactac cttgttgtct aggatgtctt     300
c                                                                     301
```

<210> SEQ ID NO 12
<211> LENGTH: 301
<212> TYPE: DNA
<213> ORGANISM: Glycine max

<400> SEQUENCE: 12

```
gtttactaac tactatatgt tttgttgtgt tttgtataac ttcattcaat tgtacaggaa      60
tgaaaatgaa tacgatttta ttgggaagat tgttaaagag gtctcccaaa aaattaatcg     120
cactctttta catgttgtgg attaccctgt tggattggag tctcgagtgc tacaggtaat     180
```
ctcactttta gatgatggtt cagacgaagt ccacatggta ggaatccatg gaattggtgg    240
ggtaggaaaa acaacaattg ctcgagcagt ttataatttg attgctgatc aatttgaagg    300
g    301

```
<210> SEQ ID NO 13
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 13
``` ataaatatt attttatttt attaaaaaga aagaaaaaa ataattttca ataacaacaa    60
cttaattatt tttatattct taatttactt gtgaatgaag cttctgatga tgcaacatat    120
gtgatgagta agaaaagag gatttcaana actcgttgat gtggaatacc gagagtatct    180
cattgattcg ttagaatacc aagaggttga tataaggggtt tgactgctcg ttgattcaag    240
agaaagccga gggttgagaa ttgagaaaaa cttnaaattt tgttcaata ataatctttt    300 c    301

```
<210> SEQ ID NO 14
<211> LENGTH: 301
<212> TYPE: DNA
<213> ORGANISM: Glycine max

<400> SEQUENCE: 14
```
tgacattact aatgtgcaca tttttgtggt taaattgtgc tttggacctg aagggaact    60 gataaaatag aattcataaa gcttgaaggg tacaacaaca tacaagtgca atggaatgga    120
aaagccttcc agaagatgaa gaacctgaga attttgataa ttgaaaatac aaccttttct    180
acaggccctg agcatctacc aaatagtttg agatttctag actggagctg ctatccttca    240
ccatctttac catctgattt caatccaaaa cgagttgaga tactcaaaat gcctgaaagt    300
t    301

```
<210> SEQ ID NO 15
<211> LENGTH: 409
<212> TYPE: DNA
<213> ORGANISM: Glycine max

<400> SEQUENCE: 15
```
ccaagatggg aaagagttga gtttagaagt gttttccaaag gccattcttg tttgccatct    60
tgatcccagg cattatcatc atcttgacct gtattatctg tacatgagtc ctaataatgt    120
catccaagta tgcagtccta atctgtatat gctctgtgat ttcgatttgt tgttccaaaa    180
gcttgcattg ggtgtcgaga aggactggtt tcgcagatgc aggaaatggt caatgaattt    240
ctcgtttcga aaaagtttc ctaagattgc ggtatgttgt tctataatat ctagattgaa    300
aagtgtcatg gaaatggtgt tgattttgaa gttcagcgta ctcatcaatg cactatgca    360 atttagttct tcatgtaatt acatatttag aacatgggac ccgataatc    409

```
<210> SEQ ID NO 16
<211> LENGTH: 301
<212> TYPE: DNA
<213> ORGANISM: Glycine max
<220> FEATURE:
<221> NAME/KEY: unsure
```

```
<222> LOCATION: (1)..(301)
<223> OTHER INFORMATION: unsure at all n locations

<400> SEQUENCE: 16
agacaattaa taagcatggc ctcntccaac tccaagaaat gctaccctct gaaatactca      60
aggagaaata tatcaaagtg ggagatgttt actgagtaat tccaataata aaaggaggc     120 ttgaacaaaa gaaggttctt ctggttctag atgatgttga caaattagag cagttaaaag    180
tacttgcggg acaatatgat tggttaggct ctggaaggac aatcattgtc accacaagag    240
agacaaacac ttgctagcta ctcatggagt gataaactta tacgaggtta aaccattaaa    300
t                                                                   301

<210> SEQ ID NO 17
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 17
attatatcta taataattta tgattatacg taagagattt tgttacatta ttcgtacata      60
attattaata aaatgattta nttanatcga tagaaaagtt agaaatccac caaaaatcat    120
tttaacattt ttttcaaatc tattgattat ttttaacaac atattagnaa ttcgtttaat    180
ttaacaatat attagtaatt tgtctaatta gggcataact ggttggattt ttttatttaa    240
aatccaagca tatactcatt ttggcccatt ggttacgcaa aaactctaca tatgccgtaa    300
c                                                                   301

<210> SEQ ID NO 18
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 18
tattgttagc acattgccct ctatcagttc atncctcaaa tctgagcaaa ctaagctttg      60
atgtctctca cataaaccga ttcaacacaa caatgtcatt ttcattgtca agaaggttca    120
gctcttttct ttcaaacctc acttcccctc cttgctttca cttagcctcc ccattgacaa    180
tgacaatgtt gttgatgatg tgttccccaa ttcaatgaca tgctccttgt gcgtcatacc    240
ccacccacca tctaatttaa caagatgtta ggatcattnt aaagatgaag cattatccca    300
c                                                                   301

<210> SEQ ID NO 19
<211> LENGTH: 301
<212> TYPE: DNA
<213> ORGANISM: Glycine max

<400> SEQUENCE: 19
gcagtcagat ccagcatagc atgaattgca ttcacaacga gacttattca tatctttaag     60
aataagacca tctaagtagg ctcttccatg tcctgaacat ggtattgctg ccacagcctc    120
agcttcttct gcagctcttg tgctccaagt tggctcccat tctcccatac atacaaacgt    180
```

```
gctaattgag gcacacaata taataataaa ttttaatttc attggacttt ggacttgttc        240
ttttggcgat tctagtcttc gtttctttgt gaaatcttca agcaatttct tggttgcact        300
t                                                                        301

<210> SEQ ID NO 20
<211> LENGTH: 1154
<212> TYPE: DNA
<213> ORGANISM: Glycine max
<220> FEATURE:
<221> NAME/KEY: unsure
<222> LOCATION: (1)..(1154)
<223> OTHER INFORMATION: unsure at all n locations

<400> SEQUENCE: 20
tgattcgcca gcttgctgcc tgcgggcaca tttctccata tcagaccaca cctctctttt         60
ctgtaagcct cttattggtt ccctaacgaa tgttgttaat tacattgttg ttctgactat        120
ttattcagct tcggttgtag ccacggattc atgacagaga ttatcaactc atgcttagtt        180
cgaagactat tttaactgtt ttagttttga gttcagaata aagcacgcag cagaggtatc        240
tatctcctca gcttaaagct tttcaattca tcactttgaa tattattttt gttttttag         300 tgagctataa cacaatcaga cttgaaaaat agtatcttat agaaaagtca attacaaatt        360
ttcttgtgaa atataaccac taaatcacat gaaaaaaata tgnaataatc gagaattaaa        420
aagttgagtt ttaggattta aggttttatc tccttttaga aataccagag ccatacaatt        480
ggtgtgcagt cttctccaat cttctatctt tattacattt ttattttgtt tttctaattc        540
tttttttaac tatttaatta gttagntttta ttttgttttt cattttttta attagttaca      600
tgacatatca caaataactt taaaattgct gactgatatg atcgaccaca tgatcacatt        660
taactgcaca agcaaattga gttaggaaaa naattataat ctgatatttc taaaatttta        720
gaaattaaat gcaaagaata aaattcaaag gactacatat aaatttggtg tattttcaga        780
ataaaaaaac atatttaatc cctctatata ataatgaggt aggaacgggg aagaatttttc       840 aaatattaat gtgaatacaa ttttctccta tagttcatta tatttcgacc gtcttaatttt      900 gtccttactc ttgaaaactt attaagctga aattttttacc tatatctaaa tgcatggaca     960
acatggctac ttcacttcag aaatctcgaa gtgcaaccaa gaaattgctt gaagatttca      1020
caaagaaacg aagactagaa tcgccaaaag aacaagtcca aagtccaatg aaattaaaat     1080
ttattattgt attgtgtgcc tcaattagca cgtttgtatg tatgggagaa tgggagccaa     1140
cttggagcac aaga                                                       1154

<210> SEQ ID NO 21
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 21
cctttaaaac gttacaccat atccattggt ggaagaggag ggatggaaaa gnaagggtcg         60
ttgcttaagg acttnttctt aggttaatga cattaatatg tgaaaattta aaatacattc        120 ttttttaattg acgttacata acatgattgg aggggcatga aaagggacag acttttagga      180
ggaatgtgat tcaatccgt ttgaaataat aagaaatata ttagaacggg ttgaatatta        240
gataatttat tataaatatt tatttttaata aaataagtat ttttttacta aattattttt      300
``` a                                                                              301

<210> SEQ ID NO 22
<211> LENGTH: 910
<212> TYPE: DNA
<213> ORGANISM: Glycine max

<400> SEQUENCE: 22
actaaaacta cctcaactgt tatagatgtg gtcatttcac ttaaatactg ctttagcaaa      60
tgtccatagc aattgttcag tgtcaatgct gctactgcac cagctattgt gttccatttc     120
ttcaaaattg gactataatt ttgtctctct ttcaatgcca aatattcagt ttcctgagct     180
aattgaagca taacttcacc tatttctttc tttgtttcag actcagcaga tttggcattt     240
gctgcttcca tcatctacag tcattaggca acaaagacat tatgatattt tcttttact      300 tttaaattaa aaagcagaaa atactataag tttgacacca ttagggatta aaaagcagaa     360
aatactacaa gcagaaaact ctacaagtta tatacatgct tctaacgtat caacctttg      420 gattgtttct taacaaatac ctacctttc aaaagcattt ttcaaggaag aacagatata     480
gtcatcaatc cggccctcag aggaattcgc tctagttttt tctccttttt cttgcctttc     540
ttcagaattt gtaacatctc ccaaaatctt ggatgctaat aacaccacag gggagaaggt     600
tttcaatttg tccaatatca ccctccctcg aaatacctct gggagttaaa gaaacctttt     660
atctgccccc ttcttggcgg gaactgagga cacatttcaa tatcttcaaa ataaccagga     720
ctccccttct ctttcttaaa ctcatttgcg ccctccattt ataatgtttg gaaggcaaaa     780
aagggaggtt taatttccca tttctcattt gtggaacatc ccctgaaaac acttgtgtgg     840 gcttttttcca cggggccttt ttttaaaaga atgtcctttt taaaaaagta tcactctcaa     900
acatgcggga                                                             910

<210> SEQ ID NO 23
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 23
tcccttagct gaaanaaaag gtcaatgtca gtatagggac atggaagtct ttcattgant      60
attactaatg gagttatggt gtttattttt gtatgtccaa tttccatagg gcatagtgcc     120
actcaattct ntaattgata tagatttctt ctgagttctc tttgtaaatt tccagccact     180
tgtatgtgca gtggtctttc attttttgg tttgctataa tcataggat taatacaaaa      240 gtgctgtttg gttagtggtt ttcaaattta cagttcagta taaagttatc caggtaatac     300
a                                                                      301

<210> SEQ ID NO 24
<211> LENGTH: 301
<212> TYPE: DNA
<213> ORGANISM: Glycine max

<400> SEQUENCE: 24
attggtcaaa ataaaacgtc cacgtgcact tgaatgatga gtttgaaccc ttattttgtg      60
tgtgtgaatg atgatgagta tgaagctatt atgtaaaaga tgatgtgaac aaagattcca     120

```
ataatttaaa aacaggcaag tggcatatat tattagactg gagatcactc aagtcaaatt      180
taatgttatt agttattact agctagaggg atagttacgg actttgcatg gtgagggaac      240
tcaatttaaa tgtaacaaga attttttattt tttttaagta acaagaaaaa attgaataaa     300
a                                                                     301
```

<210> SEQ ID NO 25
<211> LENGTH: 864
<212> TYPE: DNA
<213> ORGANISM: Glycine max
<220> FEATURE:
<221> NAME/KEY: unsure
<222> LOCATION: (1)..(864)
<223> OTHER INFORMATION: unsure at all n locations

<400> SEQUENCE: 25

```
ttgttttctt ctctgtattt acaatagggg aaagatgcat gaagcaatac gtcttgtgtt       60
gtcttagtga gatgctttgt ctcatggaca aaggagttat aaagctttat aatctgacag      120
ttttttcttt tttcttaccg aactgtctgt ctgctcaaga tggtgcatgc ttagttttgg      180
tttatggaat tcaggaagat aaggaagtat cttgaatttg agcttttaat caatttctat      240
atgcntattg tgatggtagt tttcatttaa aacaaaaatt gtgtttgtca gttggggtta      300
caatcactgg atcgcatcat ttttatgttg gatggcattc gtgtcaatat attttatctg      360
gttctgtgct aagctaccat ggaggagttt atgtcttgtt ttggtgaaat tcttctctct      420
tgattaaaag tgaagttaaa ctggaaaaaa atgagattta attaatgaac gagtgacaaa      480
tggtatgggt ttggttttttg gtttgtttat attggtttaa catgggatgt tgcgatgata     540 tagagggtc catgctatgt tctgtatgat accaataagc ttgtggtaga gtaaactcca       600
aaaggatgaa gaaaaaagtt agcataaggc atagagtgca ttattatgtt aaagaatgag      660
aaattgcaat ggcttagagt gcattattat taactatatg ctggaatata tatgataagg     720
ctccattggt ttatgagaaa ctacgggtgg agattttccc ccctattaaa tagtaacaaa      780
tttggaagat taaatacaca aatgttcact tctcttgtgt atgttggtct ctcagtgctt      840
gcatatggta gtaatctgca ttat                                            864
```

<210> SEQ ID NO 26
<211> LENGTH: 1068
<212> TYPE: DNA
<213> ORGANISM: Glycine max
<220> FEATURE:
<221> NAME/KEY: unsure
<222> LOCATION: (1)..(1068)
<223> OTHER INFORMATION: unsure at all n locations

<400> SEQUENCE: 26

```
cccaggcatt aaccagggag atggcacaaa gttgaacaat cacattaaaa ttattatttt       60
aaccagctcc accatgaac catactatca aggctctatc agtttgcttc caaagtcggg      120
cttccttaca caaacagaca agacaatgct tacataagac agacaaaact gctcatttac      180
actgtttgga agggatgaat atgggaggga agaaacacag ataacaatgt catttccttt      240
gtttggttgg agaggaagtg gaaagaaaat gagaagaaaa gttgacttct agagataaaa      300
attcaaactt ttttgtactt tctctccaat ttcaatttca aacttttctc tcctccctca      360 cttttctttcc tctcgaccaa acataggggct aaagttgcac aattcaaaaa attacactct     420
cccaaagcaa ctttgacaaa ctcaaccaat agctttgacc taactaagag acacnagctt      480
gttcacacat ctctcccca ctagaaaaga caaaactcta cagaaaaagc caaaaaccag      540
```

```
ctgcagctta atttcattta gcattgtgct tttggatcca ctataggcta ctcggatcca    600
atggttgttt caatggaatt gtgacttccc tctcttcttt gtaataaata aatctttttt    660
tgtcatcaaa tatatgtaaa acttatcctt gttaaatata accacaactt cctaataata    720
tactaccaat ttttttaat caataacaag aaaaaaatgt ctaaccatta gtcatttgct     780
atgcaagtga aaacatcctt tggaacccat gttatccgaa gtgacacgat gatttgagtc    840
tcatatgtga gaatcaatat ttaacattta attttagtag ataaataaac cccaaaagat    900
aggaggtaga aaccatgctc agatgtgtat aaagaaggtt gtaccttttg ggacttttttc   960 tttttccctt catcagcttc ttcactctct tcacttt caa catatgatac cttcctgact    1020
gtcctactag aagtgcgaat ctcactgttg cgcgaagaaa aacctgtg                 1068

<210> SEQ ID NO 27
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 27
tgttaaaagt ttaaacgtcg tataatctga aatggataaa gtgttttttt tnnaaaaaaa     60
tatttaaata ttaaaaattt ctctagagaa acaatcttat attataattg ttatcaaatg    120
gttctataga ttatatatat aagcaaaatc tttatgttag tgattctaag gactttaaaa    180
cttcaataat cctcggaagg ttataatatt ttaattctng aattacacttt tgaatcaaat    240 agttcaacag ttttgtttct taacttaaaa tcaaattgat gtttcacacc aatgagtctt    300
g                                                                    301

<210> SEQ ID NO 28
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 28
ctttgtcacc atgttngttt cacagtcacc tacngttatt tattacacaa attcttnacc    60
atgcattacc tttttaagtt naggcaaata tttttatatt tttntttacc aaatcaaact    120
ttatgcaaat taggaataaa aataagttag attactcaac gggaggcttg gccaatatga    180
cttaacctac atcaggccta tgggtcaaat tggacttttt cngaaaataa attattccaa    240
gactttcatt aaaaaanaaa aaacaaaaaa cacatatatt tcaaacttaa aagaaaaaa    300 g                                                                    301

<210> SEQ ID NO 29
<211> LENGTH: 301
<212> TYPE: DNA
<213> ORGANISM: Glycine max

<400> SEQUENCE: 29
aatttaggaa aaagacacgt atattctcta gttttttatt ttattttgaa gactttcata    60 attcttttg tttagatta ggatgattaa tcaaagtaaa caccgcccct agctttcttt    120
```

```
ttaacttgca ttacggataa cttaacccccc ttgctttgca cccaattaaa aagcaataca    180
ttcacgtgga gatacgagag tgactacata tgatttgtgg gagagaaaaa ggaataagaa    240
ggaaaaagta aatgaatgac atggataagt acatatatgg gtcctcactc atattagtca    300
c                                                                   301

<210> SEQ ID NO 30
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 30
ggaaccaaaa ctaccagatg taacaactcg tgttgaatca tcgatggctc ccatgtacct     60
cagcatacca tattcaagtt ctgcaaatcc ctgcacttca atcctcttag ttgaaggaac    120
attcaagttc aaagtctgtt aatagattaa aaattcactc atctgctaaa ttaactattt    180
tgnacattac tattggtata aaatgtcaac ctaacacatg agtcacctac taactagtga    240
ggtctcggga gggtagatat actcagctcc accctcataa gctgagaggc tgtctctagc    300
a                                                                   301

<210> SEQ ID NO 31
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 31
aacttgagtg tntntttttt tccttttcaaa tattcttccg ttctagtccc tgacctaagt     60
ctattttctt gctgtaaagg ttttttcggt cgattggagt ccagatggag agaaggtagc    120
ctctggtggt aaggataaag tgttgaagtt gtggatgggc taggctaatt tttggatgan    180
tattgggaat ccaacgaagt acaatctcaa tggagttttg cggatgcatg gatttcatgg    240
aaatcaatgg ttggtattat gtggatgcaa ggtctttaaa ttatatagac agcatagaag    300
a                                                                   301

<210> SEQ ID NO 32
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 32
caaaatgaaa tattttattt tactctnttt ccttttaat tacactcttt cagtaaaaan      60
aaaanatgcc atgtttaaa ccttgtatcc ttatttaat ttttatttat aaaatacncc      120
agatataaaa caggacgtac attctgtcat nttttaacac cttcgggcat atatgagaag    180
aggattctgt gttttgactt acacaagtac aacaaaggcc atgttgttca gtgacagtac    240
tgccttattc agttatttac cttttcaaaa taaaaaagtt atttacttgg agagtttcca    300
a                                                                   301
```

<210> SEQ ID NO 33
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 33

```
gccgggttaa gattatcctt atatccaggc ctttttattt gctnatgaat aaaacactaa    60
tcgttacaat aattgaggtg gacaatatga gatgaatgaa ttttcaatta cttcattcaa   120
cctaagaaat antgatgctt cttttcntga gtctcctcat gttctttctt ctcatgatgc   180
tcaggatctt tatgggcctt ctgcctctca tgctgtaggc atagatgatt aaacaaaatt   240
tgccatgtta tttaatattt gttactttaa aaaatnataa caattcacca aacttaaatg   300
a                                                                  301
```

<210> SEQ ID NO 34
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 34

```
tataaacatt tagatttttt atataagaaa ttattctcaa gaatccactc tgtcatgtca    60
gcttgtttca atgcaaaaaa aaatattaag gaacggtttc ttaatttcca ttaagcactt   120
ggaaagaaac ctgcattgga gntggagatg ctgtaaggag tcactcttag gtaaagcttt   180
gtgtgaacaa tttgtgcacc anaaactatt tcccttctat atatatttca gaaaccaaaa   240
aacaatttgt gcaccacaaa aattaaacta ataaaaaaaa ttataaaggt ggtggaggng   300
t                                                                  301
```

<210> SEQ ID NO 35
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 35

```
gcatggttct cgacgtttac tgattttgtg ggttgtcacc ttgtggagga cccaccttga    60
ctgtgcttgt acgaggcttc tttctatttt gagcaangct aattaaccac acattattaa   120
aaaaaataca aaattttnat ggttttttctt atttattttta ataaattttta atcaattata   180
atagaaatat tttagaaaga atgagatcac tgggaaaaac tttaacgcat gaaagcatac   240
aacttcatgc gatatagctt attcgtggac caatattggg ttaggatcct ttcttcattt   300
t                                                                  301
```

<210> SEQ ID NO 36
<211> LENGTH: 1185
<212> TYPE: DNA
<213> ORGANISM: Glycine max
<220> FEATURE:

<221> NAME/KEY: unsure
<222> LOCATION: (1)..(1185)
<223> OTHER INFORMATION: unsure at all n locations

<400> SEQUENCE: 36

```
gcatcttgag caccttgggg nattggtgct gcggctgccg gtgcttatgc cttggnnnnt    60
nattatatat cttccttcaa taatatattt tgttcacgat cgtttattta atttgaaata   120
gatttatata ttacttatgt gagatgattc acaccccctt tttatatatt ttagctttaa   180
aatgttacct tcaccagaat aaataaaaga agtgcaaact ctttggtaat cgagggaaat   240
atatatacct ccccacata tacatcatca cttagacttg gacgtatcta aatcggttaa    300
ttttaatatg tttatatgta tgcgtgtgca ttaataattt tcatattttt ttttgtaagc   360
atttaaagc cttacatatt gaaaaaattg tcattaattt gtgttttgga catgaattaa    420
tcctatcatc ttgaatcatg tccacaaata atttcaattt gacattttct тттттaaggcg   480
gccaacatat atacatactt gatctttgta cttttggatt gtgatgcтттт aataattgtg   540
gataatagat ataaaaatat attatagcta tataгtатта тттсстста cccactgtgt   600
gtaactatac tgtctataca tctcatgtgg tttgtttttt cttaatgaa aattgttggg   660
gtcatgggtg tatagagtat agtactttta tgacgccatc agaagagaaa caataaaagt   720
tcataaaaaa ttaggtgtag aaaaagatgg aacttaagaa agaaaaaga gagagagaaa   780
gtgattaagt gatgtaatat ataatgagaa atgaagaaaa agataggaag acaaataag    840
taaaaaaaag aagaaagaa agaaagatat ataacaaaa attgaaatgt atattctaat    900
atgtattgaa aacaaaatt gатсссттттт gctgcaatgg ttaatttat gacagcatga   960
gaagcatgag gccaagaaag accc agagca tgctcacagg cacaaggtag aagaggagat  1020
tgcggcagca gctactgttg gtgctggtgg ttttgtcttg catgaacacc atgagaaaaa  1080
ggaagttaag aaagaagatg aggaagctca tggaaagaag сассасссатс tgtttggctg  1140
aacatgataa atattcatat ataattaata ttcaagctcc aaacg             1185
```

<210> SEQ ID NO 37
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 37

```
ctaatggtag aggaatccac gcattctagg aaattaagct ccctaccttg tgccatatcc    60
tcatactgca cctccacatt caacattaaa tcaacattta gccnatccgc aagagtaaac   120
tttgctctat tcatcattgc ntcaacttgt tccaattttg cattccacac catttcattc   180
атттттсттсс аааатgттgса tatactcatg gccacaagat ctatcacggt acataactac   240
tggagaggat aggcacatcg cattgcacaa cgcagagggg ttcttgttaa ctcaacattt   300
g                                                                301
```

<210> SEQ ID NO 38
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 38

```
ctcctctcct cattagttgt agccctctaa gctctaaaaa ctctctcctc tcatgttcca      60
caacttgatg aaggaagagt tcaagacttc naagttagtg atgatacttc acaacaatat     120
tattcacagt tcaatatgtg atatcgtaaa cttgtttcga cctttagcaa catcctacct    180
taggtcaatg ttggtcgacg atgaaacctc actactacaa aatcattttt ttacgacgca    240
nattntaaga ctgttattaa taaccatctt agaatgtgtc acaatgacat ttttgtaatt    300
a                                                                    301
```

<210> SEQ ID NO 39
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 39

```
taactaactc tcaacaactt aactgtcatt ctttctcttc ttattcttcc tactctacat     60
tagatgattt ctcttgccta accgtttttt ctttactatt ttctttcctt ccatccaaac    120
atacaattaa tgtgcatttc acttngcttt gaacaacact taaccgttta tgctagctcg    180
aagttggatt gaggtatctt ttacgttgaa cggggactga gctttaaatc caatctagaa    240
caaataatat tttgtatgta cgtattatta tatgaaaaaa aaggttttta aaagtagaat    300
t                                                                    301
```

<210> SEQ ID NO 40
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 40

```
cattcacaac aaaagccaaa acccttttag aggctcaccg gcgaagaagc tcaacaactt     60
ctctgatcaa aatcttcaca aaatctgaca cccttagaag caaagattga aactttntct    120
caaaatcaag ctgagaaccc tgaaacaaag acaaacaact aaaaagaaca catcctcagt    180
caccaaggag tgaagaagtg tcgtaagaaa acaagggaaa aagagaagaa aaagagcgaa    240
atcactaaag acaaggatta gtttgtgatg ngaactagtt actatgtaac naggctatat    300
a                                                                    301
```

<210> SEQ ID NO 41
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 41

```
aaaagacaaa gaaagaaatn atgttaagca tncaaaactt gatgtctaag tttatgttta     60
tgcttttgnc aatgttgaag tgaagctacn tgtaaggatg ttcacgagta tgagccactc    120
```

| | |
|---|---|
| naattgaccc aaacacgttg atgtttaat gtgttttagt tgagcccaaa tcaatccatt | 180 |
| caaactactt aacttttggg ttgtgtcaca agatttaat tcttgcactc actgacccga | 240 |
| cccatgaaca tctttttaat attaaattat tatatatata tatatatttc ataatatata | 300 |
| t | 301 |

<210> SEQ ID NO 42
<211> LENGTH: 679
<212> TYPE: DNA
<213> ORGANISM: Glycine max
<220> FEATURE:
<221> NAME/KEY: unsure
<222> LOCATION: (1)..(679)
<223> OTHER INFORMATION: unsure at all n locations

<400> SEQUENCE: 42

| | |
|---|---|
| ataatttgat catcatattc ctaaactttt ntgcttaagc agagacaagc tgctcaatgt | 60 |
| gtgggtcgtg taatccgttc aaaggctgat tatggaatga tgattttgc agacaaaagg | 120 |
| ttagtatcct tgagtccttt tgcttccatg aacatgttga acatttggga aaatgtgagg | 180 |
| gttgcttata gtattctacg ctgacgttaa tttgatgaag ncaacttgct agtttctagt | 240 |
| tttgattcaa aaagcacaat gcactcttct ctttgtaact ttatggaatt tgtcctgaaa | 300 |
| tggattggaa gttattggtt gtctctaata atgaatgaca aaccaaaaga aacttgacaa | 360 |
| tcttcagaat ccagtttgtc aagcaaagaa agaaatatgt tgttcaggt ccatgacatg | 420 |
| tttagtttca aaaaccaatg taactaacag atataannag caaaaattgg taaatgtctc | 480 |
| tgtaaatatc aataattaca gtcacaaatt ctatacattn tataggaaat anccaattta | 540 |
| aacttatgaa agtctgcatg aataaatggc ctattttacc tatgatgatt gctccattta | 600 |
| tggttttggc ttctactttt ctctatgaca gtgttctgac agtaaatagt aatacattgt | 660 |
| tggttataac ttctgcact | 679 |

<210> SEQ ID NO 43
<211> LENGTH: 744
<212> TYPE: DNA
<213> ORGANISM: Glycine max

<400> SEQUENCE: 43

| | |
|---|---|
| ctaagtacga aaatcgttat ccgccgcaac agccactaag atgttctttg agtcttggca | 60 |
| cgccacgtgt cagaactgcc aacagatagc cccatctctt tctccttctc cctaaacctc | 120 |
| gaactcagca cccccatcca ctggtccctc cccactccat catttattat actttcttct | 180 |
| tcttctttat tattgttgat taatataaca tacacccaca tatttcatat gggtacttgt | 240 |
| taatttgggt gtggattgtt agtttgttac ttgttttgtt ccgttcaggt gattgtttga | 300 |
| ttgagccttg aagaaatgga ccacagcgct gatgcacatc gcacggactt gatgaccata | 360 |
| acgcggttcg tgctgaacga gcaatccaag cacccccgagt cacgcggcga tttcaccatc | 420 |
| ttgctcagtc acattgttct cggttgcaag ttcgtttgtt ccgctgtcag caaggtaagc | 480 |
| tatccctact ttgtgtgttt tttatcgaca aatattaatt gttagtatta ttaatccttt | 540 |
| ttcttttctt ctctttcgt cattagacta atcttatatc tcgttatcat gtatttattt | 600 |
| cactctattc aaatatatta ttctggtctt aaatataaga agaagaaaaa aaaatgattc | 660 |
| atgctgacta agaatgaaat attgattaga gttatgtgtt gtgacctgtg caggctggtc | 720 |
| ttgctaaact tattggactc gctg | 744 |

<210> SEQ ID NO 44
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 44

```
accaagacgg tcatagacaa cgaccntcat tgtgttcatt caatttattt acaaaattgt    60
cattangtgg cattctagga cggttcttta tgatggtctt aaaacctctc acgtaaataa   120
taattataat nncattaatn acaanaatgt cactatgtta ttttctaaga aggcggctct   180
acaaaaccgt cttagaatga ttgtcgtaga acgtaacttt tctggtagtg tctatctcaa   240
tggcaaccaa ttattagaag gnttttttgcn agaatctttg tccaattgca attatntgca   300
g                                                                  301
```

<210> SEQ ID NO 45
<211> LENGTH: 766
<212> TYPE: DNA
<213> ORGANISM: Glycine max
<220> FEATURE:
<221> NAME/KEY: unsure
<222> LOCATION: (1)..(766)
<223> OTHER INFORMATION: unsure at all n locations

<400> SEQUENCE: 45

```
attgcactcc gtgtagttgg gtccagaaga agcatttaca gaaacttcca tgtattggct    60
ataggcatgt agagcaacgt tgttcatcgc ttcaaatttt ttaatgtagg cttttggtat   120
tgggccgctg aagttgttgn aagagacatc aaaaatgact aaacngggga atccatgctt   180
gatctttaaa ccggcaatgg gaccgtacaa cttgttggct cgcaaaacca atactttcaa   240
ttctggtaga gtttgaagcc aatggggaaa cacatccttt atttgattgt ttccaagatc   300
taaaacctcc agatgaatgc aattggacaa agattctggc aaaaaacctt ctaatanttg   360
gttgccattg agatccagag ttctgagctg acagtccttt gaaaagatac ttggcaaagt   420
gccatgaagc ttgttcagtt gtagatccaa aactagaagg gatnatgagt ttgcaaggca   480
ttgtggaatg gttcctgtca acttgttgtg agacaagttg agaatctcaa ttgcacttgc   540
attgcaaatt gaggaagaga agtcaccagt gattgagtta aaactaagat caaggtaacc   600
gagttgttgg ttccatgaga attggtgcaa tgattgtgtc aataggttat gagagaggtc   660
caattcagat aacgatattt catgcaacca atttggcact ctacctttaa agttgttatt   720
ggacaaatag agcgatttc agattgggga ctttttcccc ataatt              766
```

<210> SEQ ID NO 46
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 46

```
atttccattc aacaaagtga atagtatttt ttacaaatta taattaaata tcaatanaaa    60
gattgctata ttacaattat acatcattgt ataattaa aatatataat aattgaatta   120
ttaaaattac atatatatat atatatatat atatatatat atatatatat atatatatat   180
```

```
atatnttgct gaagcaactt tacctcttca cactttctct atataggtac aggtgttctt    240
cgtgtgtttt ataaattgga cttttnttaa gntaccgtac attaaaagtc gttatgatga    300
t                                                                   301

<210> SEQ ID NO 47
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 47
tttcagtctt tattgttttc ctttattgtt tnttttact actttgatttt cttgttttca     60 tttcatatac ttttcattta tatttccaac ctttgtcttt tacacaaant cntatcttct    120
acattcttct tcattcacct aaacctaatt tcttttagga gtaatttgag aacccatcat    180
aatcaagaag catattcccc tttctttgca cnaatcnttt gattattctg ccttttccag    240
atcttgttga gactagggaa aacatatttc gtctgatttt gaattttttaa gtgacatnaa    300 t                                                                   301

<210> SEQ ID NO 48
<211> LENGTH: 533
<212> TYPE: DNA
<213> ORGANISM: Glycine max
<220> FEATURE:
<221> NAME/KEY: unsure
<222> LOCATION: (1)..(533)
<223> OTHER INFORMATION: unsure at all n locations

<400> SEQUENCE: 48
attgaaaatg agaccagtat tcattnacaa gctgattgaa tagcgatcct tctttcttca     60
tcaggcacat tggatcatca tactccacca attttcctgt caatacaagt atcccttga    120 agaaaacaag taatagtaaa aaaatattct tcacctttat tctaatnaaa attcaacagt    180
gaaaatcaag tacccaatat tttacaagtt atcactaaat caactaattg tctattataa    240
taccctttaa ccaggtgaat gcaattaaat cctctgctaa acaacataac atgcctatct    300
atggggtgtg tcaaacccag tggtataggt agaatagttt aacataacca taagaaaatg    360
gaattagagn tatgaattag cccgaaaaag gtttgttgaa tgacataaag gagtcggaaa    420 tatgcattt taccatctct gattgaaaga accatagtgc aatccatcac ggttggtatc    480
ctgtgtgcta ctgtgatcac tgtacaatct gcaaactcag tcctaatggt ctt           533

<210> SEQ ID NO 49
<211> LENGTH: 301
<212> TYPE: DNA
<213> ORGANISM: Glycine max

<400> SEQUENCE: 49
gttcacaagc gctgttggag gtacatacca aatgtagtaa aagcattaga aagctcaaca     60
aacttaacga gctcaacaga cagtggctta aaagttgaaa ctgaagcaag ttgatgcttt    120
ctagtgactt tgggtattta ggtcatcgac attataccat gccttagagt tgattttcaa    180
tcggcattgt tgttttcgac tatggttgca ttttttagtc gaccatgaaa tgtgctctga    240
gggagtaatc tagttggatt tggttctttc tttgtgtttg tctttgaccc atattttcga    300
a                                                                   301
```

<210> SEQ ID NO 50
<211> LENGTH: 301
<212> TYPE: DNA
<213> ORGANISM: Glycine max

<400> SEQUENCE: 50

```
atcatagtag gatcttgaag ttcaactgaa aatagataga gagaaagaga gaatttaccc    60
aacaaaagga gaaaaaacag taaaaataaa aaaagaagaa gaagaagcaa aaggaacgtg   120
gagtcccgtt tttgttggtt gggtttatga gggaattaga ctgaagtgtg aagccacgct   180
agctgctaca attaaattca tagtgatcat tagtcatata ttggatatct atcttgtact   240
ttgaaatgac atttcaagaa gctctgaccc tattttctct cacaaagctg ccatcaagat   300
c                                                                   301
```

<210> SEQ ID NO 51
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 51

```
tccacttagt taatccagac tgtcgatgca tttaacaaac aaacaaacat taaaagccat    60
aactgaaggc caaacactata taaagggtca ggatgcatac tttgcaaagc aagcatagag   120
cataggtcat ccaaacaacg actggtgcag cacactgaca gaagatggga acttcagcag   180
ggccgaggca ttggcctcaa ctcatctata cgttggcatt tgcctaatt gctgtcagtg    240
ttgtcgctgg tcatgataat ccttactatg cctctccacc atttaatgaa gaactcccnc   300
c                                                                   301
```

<210> SEQ ID NO 52
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 52

```
aattggaata gcgtgcaatc ttattgggtc ttactcaaaa aaataaaatt gggtcttaaa    60
tagacgtaag attgatttat aatgcattta atatttttac atttctcata catatanatg   120
tgagctttga tgtccaaaag gtgtttcatt ttccaggtca tatatgtgaa ctgtatcgac   180
ttgagattga tacatcatac ttcaatttgt ttgaggtttg acgtgttgcg gtgtgaattc   240
aacagagtcc taagtggaca taacactgat tcataacgta aagaatttaa tatttttaca   300
t                                                                   301
```

<210> SEQ ID NO 53
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 53

```
caccncaaca caagacaaca aacacccttc ctttaataat agctagtgat gaggtgaatt      60
aatttcactg ggcatggttc ataaatacgc attgcttttg gaagaaacta cacaaagtag     120
atggctcggg aaatgaagca atagctggat gttcccagcc tctggttgga gtacttttac     180
cctcattcat accattattc tcattcttct ctgatgttcg aacttgaata tgatatctg      240
cataaattgg ctgtggagaa agaacgagtg gagataacaa tggtattgcc cttgaagcct     300
c                                                                    301
```

<210> SEQ ID NO 54
<211> LENGTH: 492
<212> TYPE: DNA
<213> ORGANISM: Glycine max

<400> SEQUENCE: 54

```
atattgtggc tgcattgtct ggcatgaatc tgtcagctga tgatgtgtta gatggtgata      60
gccatttccc gtcacaggtt gagtcagatg ttgataatca tcagagatac ctatttggca    120
tgcaaggtgg tcaggatcct ggcaaacaac atgcatactt aaagaagtct gaatcaggac    180
acttgcataa atctgcttac tctgattcag gtaagaatgg tgggagtatg tcagacatca    240
acaatccatc tttggatagg catgctgagc tacaaaagtg tgctgttcct cccaataact    300
catacttcaa gggatcacct acctcagctt ttagtggtgg aggtggcgtg cctgctcagt    360
actcgccctt agatggtact aattcagcat ttacttacta tggcctgagt gggtacgctg    420
gaaatccagc attggcatcc ttggtggcta gccaacttgg aactagtaat ctgccaccct    480
tatttgaaaa tg                                                        492
```

<210> SEQ ID NO 55
<211> LENGTH: 586
<212> TYPE: DNA
<213> ORGANISM: Glycine max

<400> SEQUENCE: 55

```
tagttcattt gaatgcattg aaaaagtaca cctatgggaa gcatattgtt gctcgtgtag      60
agaaacttgt tgctgctgga ggtaattatt tcttgcttgc attaccgcta cattctctga    120
atatgtgcat gaataggaga tacacacctg aactaccctg ccaattatat gcctttagtt    180
gcatacttta ctgtttactt tgatctgct aaggtattac gttacattac gtgtagtttg     240
ccaactgggt catgtaattt gttgcagaga ggagaattgc tgctcagtct cctcatcctg    300
cttaggtggg catagaaagt tgtttgtaca gctaactgag gctagtgtga gctttctcct    360
ctcttttcct gcatccggag gttatgttta ttcctatctc aatctgtcgt gatgggtagt    420
ggccgattgg aaataaaaac actatcggtt ttaatgaaga actgtacatt ttgtagtcca    480
aagtttatac atagaagaag aatttaagtg aggcgaggct cagatgtgta atactcacct    540
gatgccccc tgcagcagag gagataaagc gacaatacga gccttt                    586
```

<210> SEQ ID NO 56
<211> LENGTH: 121
<212> TYPE: DNA
<213> ORGANISM: Glycine max

<400> SEQUENCE: 56

```
aaataaccta catcgtttgg aatattatgt cttaggttac atcaagctca aattaattaa     60
atagacctat ttgataaata cgtgtggctt gggcttattt taaaatttat tcattttaaa    120
```

| a | 121 |

<210> SEQ ID NO 57
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 57

| ttaatgtaac angcataagg gcaaccagcc aagctagaca acctcaacca ggctagctca | 60 |
| attacttcaa gtcagattaa aaagatataa attggtaggg agaaaaccaa agttttttgga | 120 |
| attgagtttc aaaaactgta tttagttttc aaaatccaac taaactaggt tgcttagaaa | 180 |
| actggtggag gggtgtgcaa agcatagagc agaatgtgca attgagggag aggttgaaca | 240 |
| aaataaaaac atcttctagc tatttcngtt ttatggtctt taaaacactt gttttttttgg | 300 |
| g | 301 |

<210> SEQ ID NO 58
<211> LENGTH: 895
<212> TYPE: DNA
<213> ORGANISM: Glycine max

<400> SEQUENCE: 58

| ttcggactcg tacgggggac ctctaaatcg acctgcagcc gatgtaaaga tcatatccta | 60 |
| tctcttttta agttttactt gacctagcta accatggcat attttgggca atgacagcgt | 120 |
| atttattatt atgagctata gatttaagta gtttatagaa cataaatcca acaatttgc | 180 |
| tcagatttct aatatatatt acgagattag aagcaagcaa gtctacaatt atcttagcga | 240 |
| gtgtttggaa ctaattccac aacgcacatc atatctacta gaagcaacaa gaagtaattt | 300 |
| ctgcatcata tgggcttggt gacgtgattt ttataggacg caattccagt ggaaattctg | 360 |
| aatatacaag cagtcaattt ttatagcatc taaagcgatt cagtaaagcg caacagcaaa | 420 |
| acaccagtct tatatcattt atcgcttaat ggtgaagctg aagaactcta agaaacgca | 480 |
| atgtgaaaat agaatattta cataaataaa aaggctaaat tgtttctttt gccccctcaa | 540 |
| atatgagaca agaatcagtt taatcccata acatattgaa gtcaaatcat gacgggtgca | 600 |
| cagacgatga ccgtctatta ctttccgctc tccttttttct cttggctgga aattgtggcc | 660 |
| aaaatacaat attttttttc ttgtcaactc gaatggagta agatgggatc aaatcaaatt | 720 |
| gacaatgttt tgtgggatac aaaataattt tacaagttac aaccacacac gcaagaaaag | 780 |
| aaaagtgaag aatgggacta aaacgaaact ggcctaatga ggataaaaaa gaacacttca | 840 |
| gtccaaacca ataataaaa gaagcttcag gttagcaaag ccagtcttga tggca | 895 |

<210> SEQ ID NO 59
<211> LENGTH: 484
<212> TYPE: DNA
<213> ORGANISM: Glycine max

<400> SEQUENCE: 59

| tggaaaacga atcaagcgtt gaattggttt gaatttgcat cccaatccaa ccaacgtcgc | 60 |
| aatttcattc ttttcatcca ataattcaat tcaccaatgg agcttttgaa gcctttgcac | 120 |
| cctcaccatg cacccatttt gcgaattccc tttcacgctg ttccctcctc ctcttcttct | 180 |

```
tcttctcaat ctaaggttcc ccttcctatg atttctaagg ttcatgtagc tgttgggaaa      240
tcgctcgaca aagctgtccc cttgcttcga tggactttaa atcacttccg gaacgcggaa      300
atcgtcattg ttcatgctta tcaaccttct ctcaccatcc ccactctatg taagctcatt      360
tcattcaatt ttgattctga attttcatga tctccacttt ttccccccctt ttgcgctaat      420 tgattggatg tatttgaatt ttgtgcgttg aacagtgggg aaattgccag catcacaggc      480
tagt                                                                  484
```

<210> SEQ ID NO 60
<211> LENGTH: 1056
<212> TYPE: DNA
<213> ORGANISM: Glycine max

<400> SEQUENCE: 60

```
aaagaaatat gttctgcgta agggtcgtga ttcagagtat gcatggcatg ttgtccaaaa       60
tcatgcagac aatgcattgt attgtgaaac acctgccagg gcttttttaga aagtgaatct      120 gggcatttttc ttagatgctt gtgattgtct tttaacataa ctgaaaagaa ttgtatatat     180 ccctttttaac acttttcata ggatccctgc tcacctaacg cttttgatct tttggccata    240
atgcattact aacaacactt tcaacattga gtgcccatat taataattga cattcagtat     300
ttcccttgct tttccattaa gtacctgata tcacatcctt atttcctctc tccgctttaa     360
ttttaaataa ataaatccgt tgcgaaccac ttggataaat gagtataaaa tctgagaaa      420 ctaggcttgc atgtagatta ctagatttct cgtttgtggg gttttaaata cgtatgcgta    480
agtgatggca atactgctct taaaagtgaa ggctctactg ccgccacctc cttcgtggag     540
cagcacaatg cctccgcaat tgctccaaaa aggaagaaat attgaattgc tacttctgaa    600
tcgaggacat caaagtcatt acgatatgac aaatgttaaa ttaagaaatt taaagtaaaa    660
atatttttat tgggaaatac aatattatat tattcattgt ttttttataa tttatataat    720
aaatattttt ttaatttcct aattcatgtc ctaaaaataa tttaataaga tccataagaa    780
attagtagtt ttttcttaat tatgaccggt tagtgtaacg acacaatgat tctgtttctc    840
tttattgtcg acagagctat agaaaaagct gatgagcatg gctattggct attgcaaatt    900
aatgataaag cattctcact cgttatgtca ctctttttga ccccattctt gctctaattg    960
gacttggatt ttaccaacag cgtctcttta ttcacagttc ttggcaataa ttctcagttt   1020
ctatgcattg cacagaacaa caaggagtgg acgatt                             1056
```

<210> SEQ ID NO 61
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 61

```
aagactgcag catgtcacta caaattttgc tgtttgtaag acgattgaat tgaaattctt       60
tcctttattc tggttatctt ttcaactttc ctttgttaag tgtctttgag aactgagctt     120
gaggaatttt aattacatag tccggaatca tcatgccatt tactctgatg caaggtgtac     180
acacaagtga tgatgtgaaa ttgattcaca atatctagtn gaattttgtt tngaattgta    240
taattcanct tgtctggagc tagaactaat ctgtagttag ttttacatga ttattttctg    300
c                                                                    301
```

<210> SEQ ID NO 62
<211> LENGTH: 301
<212> TYPE: DNA
<213> ORGANISM: Glycine max

<400> SEQUENCE: 62
tataggatcc aaagctagat cagctgaatg ataagggcag agtcagcaaa agggcatttg      60
agaagagaga gaaagcgcaa gacaaacaga aacacacctt gggtaactag tccgaatgga     120
gagaacaact tcttgagctg ctcctgtgta gtgtaaagca taatcatgaa aaatgaaatg     180
aagcaatggt gagagagggg ttgggcttca atttattgaa gagagggagg agagaagaac     240
cctaactgtg gacgaagagc tttgtcccga ttctccgtga catctccact ttccgattga     300
t                                                                    301

<210> SEQ ID NO 63
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 63
aatatatttt tggtgataaa aatganagtg gaaaatatac aagtatgtca gtcaagttga      60
atacggctag tgaataattc aatgaacatg anagatatag gaattattaa agatacaaga     120
ataacaatta ataattcacc taatatattt ccgaaaatgt cttacccctc ctaataaatg     180
tggctagcta gcaatagaaa atttgtaata caaataagga taaatagtna cttttgtttc     240
ttgaaatagt cacttttgtt ttttgatgtg taattcattg ataaatacat ccctaaaagt     300
g                                                                    301

<210> SEQ ID NO 64
<211> LENGTH: 301
<212> TYPE: DNA
<213> ORGANISM: Glycine max

<400> SEQUENCE: 64
aataaagaaa aacaaaaaaa atattattat agtagtagta taaattagtg tttgaattgt      60
tatctgtatg actgtatcat atatttaatt atatccgttc tcattatata agagttatat     120
atattgtaat atctccctcc ctccctcgaa agctaaacgc ctacatggcc caactctctt     180
cagagtcaac gccacctaaa tctaaacgtt attttctgta gcacacaatc agacagcaac     240
cctttcatgt gtgctgcaat cccatgatta aaaattggcg gtcaacggct acgctctcca     300
t                                                                    301

<210> SEQ ID NO 65
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 65
gncatggctc cctggngtta gaggnggngg caatctcgtc gacccagaat ggcttgatgg      60

```
atcgtgagtc cacccnaatt ccttcccnct ttttggtttc aaaatgtgtt ttctataata      120
attccatgca tattcagcaa tccatttgtc atattctgaa aattgtttct aaaattaagt      180
gttttgtggt ctgagcttac tggtgtgagt catctgtatt ggtgttgaat atggtcctaa      240
cttaagggtg tgagtcattt gaaatgatgt cgaanggtga ggcatgaact tggtttagtc      300
t                                                                     301

<210> SEQ ID NO 66
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 66
aggtatttat aagtgtggtt tagtcaactt tgggtatct caaaaaaaca aaagtcaact       60
tttggagaaa gagtaagcaa agccggctac atgcaatgca agtgtattga atgatgata     120 tggctaaggg ttcacataca tatgaaaccg ngctcacggg ttttgtcttg tgccgaggca     180
cggtctactg tgatgcngct agtgcaaata aaatgatac cgcgtgagag tgtgtattta     240
gtcaaagttt tccatttggg tgaccaccac accaaaaagt agagctttat gcgggaaagc     300
t                                                                     301

<210> SEQ ID NO 67
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 67
atatggaaca taccttnct gactcacccc ttatgtgcac aaagcattat gattcaagct       60
ttacaaaatg aaagaattct aaatctctgc catttcaaat tccttgcaat ttgaaatttt     120
ctcatccaaa acacaaggta aagacaaatg tcaaattttta actgttatac cggtacagct     180
ggcaactggc acctgggaag agaaataact caagttgaag ctaacaagct ttaatttgtc     240
cagaatttca tgatgaaact caaatctttt gttaccaaat tcagtttata tgctgtagtt     300
t                                                                     301

<210> SEQ ID NO 68
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 68
atttaaacat aaacatggca ttaatgaatt actaacactg gggctcggct atacacaggg      60
aaggaaagag aaaaagagag agtagattaa tcgataaaga gaaacaaaaa gaaagaaaa     120 acaacatagt atgtagatac ccaaatagca tgtggaagta agatttagtg gccagctgac     180
cacgtgattt ttatattgct atagactata ataagtgcc cactagtgtt tgtataaact     240
tatgtattaa tattaantca tgcatggagc tttaatataa gctatcggct gngtttatga    300
```

| t | 301 |

<210> SEQ ID NO 69
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 69

| tacggccaga ttctgaaagc tgcttcctag aaagtaccta ttgctttat tcacggtctt | 60 |
| cataatcact aagtggattt acttcggata ttgtctggta ataattatct accttgggga | 120 |
| ttttgctgtt gaaagancat catgatatag atttaattaa atagtattgc taattaatgc | 180 |
| taatgtttgc tttggaccgt acaggagaat ttcaagtagc catcaaaaca gaaccggagt | 240 |
| gatggtctct ggtttatta taatggaagt tggcggtacg tcaaatttgg cttcttctat | 300 |
| a | 301 |

<210> SEQ ID NO 70
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 70

| ttaactttt cattttatt taatataaaa tttcacctca aacttataat tcaataatat | 60 |
| aagcttgtag gcaaggttac ctaagtgaga tnagttcata ttaaaagtgt gaatatattt | 120 |
| cagtgtgttt gtcggaaatg aataattatt ttcctttcct agttaaccaa ttgctcataa | 180 |
| caaactttg ttcgtttggc aaaactcaaa ttgcaacata ttccctcatt ttngttaaaa | 240 |
| gagaaaattg ccatgaaaca gcttgaaaat tgaatacaca aagggagact atctagtatg | 300 |
| t | 301 |

<210> SEQ ID NO 71
<211> LENGTH: 1102
<212> TYPE: DNA
<213> ORGANISM: Glycine max
<220> FEATURE:
<221> NAME/KEY: unsure
<222> LOCATION: (1)..(1102)
<223> OTHER INFORMATION: unsure at all n locations

<400> SEQUENCE: 71

| gtttcgccag cttgcactgc ctgagatgaa gtaattgctg ctgcggtgct gctccggcac | 60 |
| cgccttgtgc tggtgcccgg ccaccaggta gagcaaaaga tgtcactcac tctgttcatg | 120 |
| aaaaatgggc tcaaggtcaa tgtgcatgag agggatttga gaggggttat cacaagtatt | 180 |
| aaaaaggaaa gggaggaaga tgttgatttg agaagtaacg aaagttagtg tggtgttcaa | 240 |
| tagatgaagc agagggtgtt ggaggttttt gaatgtggag acaagttcaa atgagaaaaa | 300 |
| ttcagaccct ggggctttag cttatagaac aagagaacat aatttccttt taagaaaagg | 360 |
| gtatattcag agtatttata attccttatga taaattgtgg atggattctt tttccagggt | 420 |
| cgtgggatgg atgattgctt tctcaatcca tcgttccttg tagaatcctt gcaaatattc | 480 |

```
attgtattct ttatttcttg tcggttttga tgtttctatt taattttact ggtggtgaga    540
gctaaactca catttcacaa tgttgaatgt tgatgttcat aaaagaatgc cttacgtttt    600
atgaaagtat aatgatcgga tttgactctt ttgtcatata aatggatga tgcttaagtg    660 gtagtggtat actcaaaaac tgcaaaattt agctttacag ttcatctgca ttttttggtg    720
aatattcatc tgtgatttta gattctgttt ccaggatcct tgcctatgac aatgaaattg    780
aaatgcacan attgaaccag tagtaaaagt agatatactg atgtcttttg ttaggggaca    840
ttgaatcaga aaactgtgcg accaattttc tcagccatgt atgatgaaga agcagagttg    900
gccatataac atgtatttta actttaagca taagtatgct tgagttatat aagtggacat    960
tatccaccat ctatacagaa accatttaga tcatgggaca agacatttgc aaaaggtgcc   1020
tagttaatcc aagatttcta gataaaatgt aaaggctttc agctatttga tcaaaaactt   1080
tgatggttgc tctcttcgat tt                                            1102

<210> SEQ ID NO 72
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 72
tattttaacc aattagcata agagacaata aaaataact ccataatatt aacaagattg     60
tgacttaagt tgcctatcca caatttgnaa aataatttat caaaatgcaa gcacaaaaat   120
aaatttacga aattgaacaa atgcaattt ttaaggaaat aaacattgaa atgctatcct    180
tggattagtt ttaaggctct agtggtacca taacttgatg tgccgcacgc tcacgtattc   240
tacaattcgg ataagaggta tagactatag agaaatattg tctgattttt agtttctctc   300
a                                                                   301

<210> SEQ ID NO 73
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 73
aaatcacact ttactctcaa gtgcactttt gcactttata atatccaaat tnatatataa     60
tttttccccc acttagaaga gacgttaaat gatgtcagtg ttgtcaactg ggtactctaa    120
ctttaatatt agtctgtttg gatataagtc ataagctctt ttgagagttt ctctactaaa    180
aatataccat tttcttgttc tcatgccttc ttcatgcttg aacttgaaca tcccttaac     240 aaatgcagga agaagtgcta gttaatgcct ccgtggtgaa aagtggaaga aaattgactg    300
t                                                                   301

<210> SEQ ID NO 74
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations
```

<400> SEQUENCE: 74

```
tttgcttnca ttttacttag ttattacttg agattttcta tgaaaatgca tgttttaaca      60
agccgatgat ttcttcaatt gcttagcaga tatantnatt gtcataatgt taagagtagc     120
tacatctttt caacaangtt aaaatgcact actaagcatt taaacacaca ttagccaaca     180
agtccatttt ctgcaatgtc ttttccaatt taaatgactt ccaaaacata tgcactcatg     240
ctccaaatca agtaaaaata tcttcaactt tttttcatgt atatacagac agagaaacac     300
c                                                                     301
```

<210> SEQ ID NO 75
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 75

```
tagtgaaata cgtaatgcgt tagttgaaga gaacaaaagn ttacatgttc anatatcaaa      60
agtctaacaa tttggctaca tgcccaacac gttatgcant ggagatgagt gtactataaa     120
gggaaggcca atgtatgcag gtgtattcaa tcaatgtttg tcaaatctgg tgagctaaac     180
tgatgttggg naaattttan agaaggaggt tgattttgtg gttggaaaag aaaggtttga     240
aggacggagt gagttcaaat tttatcacta atattttaat aaaaattaat aattaaagtt     300
g                                                                     301
```

<210> SEQ ID NO 76
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 76

```
ttaaataat taatatttta tgtatgcaac cttanttaac ccccaatgtg tttctttcct      60
tgggtgtgac tcgacctaag tcagtgagtc actngactaa ntgcaaacnn gattgggtta     120
cactaagttt aacgcttnat caatctgata ggcaactcga ctcagtcaaa cttttgagtc     180
gcagtcaaac cagttcaatc agttgggttg gtctngatttt taaaacatta tcaccaccat    240
cactattgtc attactacta tttcaccccn accactattg tcattgctag caccaccatt    300
c                                                                     301
```

<210> SEQ ID NO 77
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 77

```
tcttcataaa aaagacatcc aaanaataaa ttctagatga tagaaattta aattntatga      60
taaattattt tncttaatta aaattcttta tccaaataaa ntctagatat tttngggaga     120
```

```
aaggaaatga tttatttcta ggatagagat agtgaagatg gtcctcccac atgtgattct    180
aatttgggct catatgtagc ttttagaatc cacgtcttat cctttttgtcc attccatctt    240 gctacttctt cctcttgaac tgacaaataa cattcttaaa gagcagcata attcttcaaa    300
c                                                                    301

<210> SEQ ID NO 78
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 78
aggcaactta actaacaaaa acaaatttct aaagtaaaat cagaaaacac aggtagcaat     60
tctgagctta accataataa aaacaaggaa taaataaatg gagtcattta cgaaaattcc    120
tttattgtta atatgaaaaa aagaaaataa atttctgata gaaacaagtt actaatacta    180
tgaacagnaa caaatgtgag aacacaagca cacagtacac acatggcatg tgcgcataca    240
tttgccaatg tgagcttata gccttctact ttacaggcac atcttcctag agacacatgc    300
a                                                                    301

<210> SEQ ID NO 79
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 79
gtggatgcca tgtcaaaaga aggtgtttca aggatgaatt ttaaaatttt catattcctc     60
ttaaccacat gaattataag attccctcta cgggtctgaa ctanaaantt tttcatattn    120
cttgggttga ataaacctga ctacatttaa aaacagccat cacgagccaa cccttcgcta    180
tgagcctact actgtaataa ttaagaggat tttccaaaca aaaactaaaa attttcacgt    240
tcaacaaagc aagctagcta acttgaattt aaattgatgc agtgtaacct tctataaact    300
a                                                                    301

<210> SEQ ID NO 80
<211> LENGTH: 301
<212> TYPE: DNA
<213> ORGANISM: Glycine max

<400> SEQUENCE: 80
aagtgcattc ccctcatatt tctatcgacg tgggactcca tgataggtaa atgatttaa      60 taactgataa ttcaagcctc agtgcaggac atgagggtat ctatcgatgt gagacttatt    120
tagagaactg ccattgttaa actgatgata tagatgtggg actacttctt atgcctcaac    180
atgatgtggg agtgggacta ttgctagctt aatatatgct tagtttaaat cactactcac    240
aattaaaata gtccttgcaa tattcaatat tttagctttg gtccttgttg ttacttaatt    300
t                                                                    301

<210> SEQ ID NO 81
<211> LENGTH: 301
```

```
<212> TYPE: DNA
<213> ORGANISM: Glycine max

<400> SEQUENCE: 81
caatatggca tgtttatctg gtaagcgtag ataattagtc tgaaactgac actcaaaaaa      60
ctttaagcca acgttatgtg aaccagtcaa atcagtatca taaaaaaaaa cagtcaaatc     120
agtagggacc aatcctagca aattagacca ccaaaaggga ttaattacaa aggagaaatg     180
attttcttgt aattaatatt ccaactaata tggcattgaa caggaagcta gagaaacatc     240
ctaatgagga aaatagtagg gcaaaacaaa ataaaaataa tgcccttctc tataacagaa     300
t                                                                     301

<210> SEQ ID NO 82
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 82
actttgtcaa aagaaaagc tttcccatgc ctgcattgga aagactaaga gaaaagnagg       60
gttagcttgt gtgcaagtta caaattttac tcatacattt agtttgcatg atgagctgta    120
caattaaggg ttcagataca tattggcaag tggcaacaaa gggaagttgg aagtgaaaca    180
gctactattc tcatcgttcc taaaatgttt ctttcattta acaaaatgaa tttgcaagag    240
taaacatatc acagaaggca ttaatcaggt gccataatca gggcagagaa taatttttaat   300
g                                                                     301

<210> SEQ ID NO 83
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 83 aggttttgg gcttagcgca cangtgtgcg ctgagcgagt tatgcaactc ttattggcct       60
gcaactttcg ttaagtagga catggctcac ttatcgaatt aaatgcctca tgatgcagta    120
gaggggtcac gctagcgag atgggctcgc ttagcgctat gccattttag agagagttat    180
gggcttagcg ggtatggtac acttagtcca atagccatga aaatccaaga agagagcctt    240
ctacgcttat cgcatagaca cgcttagcga gagactatgt cgcgtttagc cctattccat    300
t                                                                     301

<210> SEQ ID NO 84
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 84
catantctta attcgaatgc tattttcttc tttgaaacgt tgntttattg taagagaatt      60
```

```
gaggaaataa aataaagtta ggttttgatt attttttntt gttgattgtt caggaagaaa      120
tgatggttta acttttttttc tgtaggaaac ctttccactc tcaacttaat aggtactcta      180
gacaagccaa cttggagact aattggtttt tatggattcc cngagaaaaa taggaggaag      240
gattcttgng attttattga gaactcttgc ataggatcat tctctcccnt ggtgtataat      300
a                                                                     301

<210> SEQ ID NO 85
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 85
ttggcaagga cctatttttga gtctctctat tctcgtgatg acggggacca tgcaaaacta      60
ttttnttttt tttattcttc agtaaatatt agtttgaact tttcatgttt ttacaattta      120
ttataaaatc taattattta tataattaga gtaaaagtat tttcgtgtat gtttcacgtg      180
tgtgtagtga atcaaaacta acataattct acatagatag atagatagat aattttttta      240
cagaagtata cacatattta atctgctatt aatttatgta aagaatgttg cataaaagaa      300
t                                                                     301

<210> SEQ ID NO 86
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 86
catatcctgc aagataagat agaactggaa atcttctttt tcaataaata gcgatcaaac      60
aatgaactta aaaatccttt agtcttgttt atcttagatt tatgattaag ttagtgaagt      120
gttttaagat aaaatatcaa acttattgga attgatattt ttttgggtat ttaattgagc      180 attttttacaa gacaacgatg ttcgggtacg cccaatgtgg tagttaagtt cttgaatttt      240
tggcagataa ttaatcatat acacngtcaa taaaaaacat ccttatttca aaaatatatg      300
t                                                                     301

<210> SEQ ID NO 87
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 87
tagaactctt tttcttattt gtcttgatca aagaatgaaa cccaatatat gtatataggt      60
aaatgctgtg gcataacata agaaattaaa gtgaaaaaaa taaaacggta atttcatttt      120
caacgtaatg ctttattaaa cagaaaagaa gagaacccco atctcctcaa ttatatgatt      180
aggattaggg cttctgcgtg tgtaattatc attcgccaaa aatgacatct ttgttaccca      240
gctattgcgg gaaatataga tatattactt atgagaaatt aaagctgcgt acattactca      300
``` a                                                                           301

<210> SEQ ID NO 88
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 88
gcgctggttn tcttcgcttg tacaaacgaa agtaattgtg attactataa aataggcaaa      60
taacaaatgg tcagtgatgg cctcaaactg ggatgcttgt caattttttgg ggcagggtct    120 ttcacatttg atgaaccttg ttggctatcg agcagggtat ttccaaagtt tggtctgcaa    180
aacagattac tgagaaacca tcaattngac caaatattta gatgtctatc ttcaagctca    240
aggagcgatc ataacagata tcaaatgtct tgaaactcat gggagttggt tactgatcac    300
g                                                                           301

<210> SEQ ID NO 89
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 89
tccttggtgc taccgtatac cattttgtat tttcaattta cagttgtcac atgttacata      60
aaattctgtt cctcttaaaa aattatttgt gtactgttgg tctattaaat tgtcatagta    120
tgtatgtatg atagttctcc taacaagaga tgcaaacagg ctagtaaaga tgcagcgagg    180
aggctgaaaa ttttgggcct agtcatcaca gtttagtcat gtttcactct tgggatgtag    240
tagtattaat taaaatgttc ttataagact tgaacaatcn ttcttaattc aaataaaaat    300
a                                                                           301

<210> SEQ ID NO 90
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 90
ttcccctatt ttttatgtag aaaaaatgta aatatgcact aaaaatttta ctattttcat      60
taaaaaaatt gataatttta attttaaact ttatacattt ttagtgcaca atgccactat    120
aaagtttgnt ttttttttccg tcaagggtgg ctgaaggcca tacgaacaga acggggggaat    180 gaaacccccta aaaaagttt taatctcaaa cttttacaac tagaaccacc ctaataggtt    240
atttaaatta ataaaatata ataaagttaa tatgaattgg taaacactaa ttaatgaatt    300
g                                                                           301

<210> SEQ ID NO 91
<211> LENGTH: 301
<212> TYPE: DNA

```
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 91
gacacttgat cgttaataga nanatatata tatatatata tatatatnna tagagagaga      60
gagagagaga gactttttg agtaacttga aagggtgaca atgtaaaact ataagaggat      120
aatgtaccca aattataatt acaaaaggga gaaaatgaag atcacatcct tgaccaaagg     180
ggctatatac tgatggcacc atagcaatac aacatggtga taaaacatga cattttcaac    240
aaggcttctg aaattctaaa gaagtatttt cacactaaaa gaacaattgc gaatatttac    300
t                                                                    301

<210> SEQ ID NO 92
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 92
aaggagttga gctctggtaa ttaacgaatg caacacaana caagtgagtg aagagaaaaa     60
acggggttgg gttgggtgcg attctgaaan tgacggaaac gtcccattca cgccaacaca   120
ctcatnatta accaactaac ttcaactaag aaagtgaaac ctctcccctc cttacctttg   180
cttttaccaa tgtttccttc cccaaccaaa caaccacaaa tcttgtctcc ttacttccca   240 tttcttttc tcttttggt tttattcttt acaatatatt aatttaattt taatcttttc    300
a                                                                    301

<210> SEQ ID NO 93
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 93
ttactcaaat tttctcctcc tttagttagt tgaatncttt ctaggctgat tggtgattcg     60
gattcattat tagaggctcc acattggatg acagaggcct ataacacatg ttgaggttgg   120
ttcgaggtgg tgaatacata aaacatgatg gaatttgata actttaagtg gtagggggttt  180 ctcattggat gaaagaggcc tataccactt gttgngattg attgaaaatg gtggatacat   240
ataatgttgg aaaatttgag aattgtcatc ggtaagggat gattgatttt gcaaaagatt   300
g                                                                    301

<210> SEQ ID NO 94
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 94
```

```
ttgcaatctg actcaaacaa tatgttgtta atattgagct ccctcctgca gcagacccat        60
tgctcgaata aattggccat ggtcatcacg taagtaagat tcctattcca aagcactgct       120
gctgttaaaa tatgttagca tcttgcgttt aatttcacct tttggagtgc tgcatttgct       180
gttgttggaa gtggcattat atatgattcg aatcatatgt tttgttcaat attttttatg       240
aaattaatct tntaaagtga ataaatattt ttaaataaaa atatatttac cattaattta       300
a                                                                      301

<210> SEQ ID NO 95
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 95
ctgatattag tggttactat cgacagccga caggcaaagt atcatcgatc cacaaccaac        60
tgaagaaaat aaaattagtt ttttttttat tatttacata agtaacaagg gaataacgat       120
aaaaagtaaa aaaaatataa aagaaacttt ccactacata gcctataatc tagtgtcatt       180
tttgggctct ctttccccac atctatcaac aacattgacc atattaaaac atantgttgc       240
aatgatcgaa aatgattttt ttcacaataa ctaaaaataa aagcaactat acctttcat       300 a                                                                      301

<210> SEQ ID NO 96
<211> LENGTH: 301
<212> TYPE: DNA
<213> ORGANISM: Glycine max

<400> SEQUENCE: 96
aaatagaaca aaatgtttta gagaattcag aatgagaatg ctttcttatt caagagaaca        60
tgaaatccat ctaggttaat attaattcag cccaacttca taaatactaa ttcccacgaa       120
cactaaatgc atcttatcat gtgatacata tactattacc tagtgcattg actcttataa       180
tttccagcag aaacagcctc accgattaaa ttcaaaatga tgctggtgaa gtaatagacc       240
taaaaattac taaggtaaag aaaaatacgt aaaacagacc agaaaaataa aatacaaaga       300
a                                                                      301

<210> SEQ ID NO 97
<211> LENGTH: 301
<212> TYPE: DNA
<213> ORGANISM: Glycine max

<400> SEQUENCE: 97
gcattaatga aaaatggagt acacggaaaa gatcacacgc aaacaatatt ttgtcaagga        60
aaacgccata cctatacata cacagaaaat tcatatttga cagggatgga gaaaaacata       120
tctgtaccta cacaagggat agacaggtaa tcttccccca agcttcctcc ttcttcaagt       180 cttttttctct attatccggt atttcttagc cgggaaggca ggatacctgt caaaagtatc       240
ccaatgctca agttatatct cagacaaaaa aaatagaatg cgtacttaat gtgatgaaca       300
a                                                                      301

<210> SEQ ID NO 98
```

```
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 98
acgattattt atcttttctt tgggaacaag tcccttaaa tatttaaatt tctaatgtaa      60
aaaggtccct aatcaancat tgtttttaa tttttatagt aatttagcat agaaantcaa     120
tttcacaatt gctaggaagt tcttttaagt gaattaggaa cccaatngaa ggacaaaagc    180
ctccctcaaa tcaattgcta agagagaatc atctgtggtt aatccgttgc taccgctgaa    240
cagacgcaaa attcacacca acaaattcat acaaaaaaat atgaaagtaa agagacacaa    300
c                                                                    301

<210> SEQ ID NO 99
<211> LENGTH: 495
<212> TYPE: DNA
<213> ORGANISM: Glycine max

<400> SEQUENCE: 99
ggagttatat ttcttgtttt aagagcacca acaaagaaa ctggattctc cacacacgac      60
aatcttgttg atgtttcctt tgaaaaaata tctaacaagc gttcattttc ataccaatag    120
gcagccatac tgaactttcc tctcagaatt atactttcca ttttcatacc atgggcagtc    180
atttgtttgg caatggtggt aacttgctct tcctttgttc cttcatcaga ttcttttgat    240
ggacataggg catttgtaat aagacagaga cgtttctttc ccttgtttgt cattccaaat    300
ttttttatta acatatccac gccaacaatg acaacatcaa gaactaacat caaagtcaag    360
gtgatatgat cagggataaa aacaagaaca atttagtaat tcctagcatt cgaggtctag    420
gaacctccag agaagaagct aagaaaggga agttttattt tctgcttgct tcatcacgat    480
acatcattca ttctt                                                    495

<210> SEQ ID NO 100
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 100
aaaactccga taancattan aaccggcgat aaaaatgagt gatcaaaact acacattaaa      60 ngcactttt tttaataata aaaatgttag gaagaatgta cgtgatagta gtaaggaaga      120
aacaagatag ggctagcttc ggatgtacgg ccaagagtgg aatcttgttt tgcagctcta    180
tgaccagttt ggtttattca tcacaggaag gagaaatgga agatgaaac acttgctatg    240 gcatgctacg tgttggtgta tgtggaatgc taggaacaac atcgatatca tttgtccgga    300
c                                                                    301

<210> SEQ ID NO 101
<211> LENGTH: 301
<212> TYPE: DNA
<213> ORGANISM: Glycine max

<400> SEQUENCE: 101
```

```
ttaatattta atagattttg aatgagaaat tgattgctga gtactgtgag attgttttag    60
aaaacaattt ttaatattta taaccaaaaa atgagaatgg aatcaaatag gccctaaatc   120
ttttacaact taatgaggac tatacaatcc acttgtttcc tcatgtttca tgtcgctgaa   180
gcatgtgacc aacttggtta ctgtgtaaaa ctcacttcac aaaacatgtc atttatccaa   240
atatagagga agatgttgaa cgctaatgtt tgtacagaaa ctgattctca aacttccttt   300
c                                                                  301
```

<210> SEQ ID NO 102
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 102

```
actgctcttt tttcccctac ctacctgcat acgatgttat ctacttctac tttacaagct    60
tcattgatct cacttcaact gcttcaattc agatggtaat aactaataac tctcgatcga   120
gagccaaata atgttttgag ttcagtttca ccatgcacca tgcccatctg ttttcgtaat   180
ttgatggatc taagaagcaa atttgctctg tttttttactg tatacgtgac agagaagtaa   240
acacgcactt gatccaattc ctttcgtgga aatcaacagt antagcaaca ataaaacata   300
t                                                                  301
```

<210> SEQ ID NO 103
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 103

```
ttaaattatt aagaaattta tcttttttttt tcataaaagt agttctaaaa aagcctatcc    60
aaatatcttt gttggtgttt ttactgacaa aggaatgcga agttttggtt gctttggatc   120
aattgaagta ataagccggg aagcttggtt tggaaagatc atgtgtttat cggacctctt   180
gtttgaaaac atctcatgcc aaatccaatt cacattgcag gcttagcgtg aaggagtcca   240
aaccacaatg gtgtttcgtt ttttgtcatg cttatcgctt gtttttgtat tggntttatt   300
t                                                                  301
```

<210> SEQ ID NO 104
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 104

```
ctaaaaagat ctaaattatc atttcttaaa atatctcaat taattcatta ccatcatgat    60
tgacgttatc attaccatga gcatccttgc attcatcacc ataaatcatc attgtcatca   120
cctctgtcac catcaccttt ttgtcatcat cgtcgttgtc atcaactgtc accatcatta   180
```

```
tcgttgctat cgtcattacc accatcacaa caacaatgac aagatcatga cggtggagnt    240
gttgatcgac ttacaaaatt ataagaatat ctttctaaaa ataactactt ataaactttt    300
t                                                                   301

<210> SEQ ID NO 105
<211> LENGTH: 301
<212> TYPE: DNA
<213> ORGANISM: Glycine max

<400> SEQUENCE: 105
tttatacact taacatataa ccaataaact cttatatatg taataaatttt ttatttatga    60 caaatattta ataaattat atatttataa tttaaatttg agttcacaag ttatattaac    120
tatcggttaa ttaaattaaa atcattttac actggttaat gcacacacta acaataataa    180
agttgataat cagattttttt ttttcttaaa aaaaagaac gacaatatgt tgcctccagt    240
ccatggaaat gtggaattct tgatttgatt ggaagataac aaataaaata tgagcaatga    300
a                                                                   301

<210> SEQ ID NO 106
<211> LENGTH: 301
<212> TYPE: DNA
<213> ORGANISM: Glycine max

<400> SEQUENCE: 106
aaaatggccc aaatctcctt attttgcgaa ttaaataaca tcatctatga tttagcaaat    60
aaagaatgtg attttttata tattttttaat ggattaaata atgtgattta tctcctaaat   120
attattatta ttattattat tattattatt attttatgat agggttgggt actcacatac    180
ccataaccac catcgttttc attaaaattt gtggataatt agtgtacctc agctcataat    240
ccattaagtg gataattact ttatttatga tggataattt ttttgagtaa tagtagaatt    300
t                                                                   301

<210> SEQ ID NO 107
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 107
ttttctaaat tataaccaca gaagtgtcta atgcaaacaa ttngatttgc attattctttt   60 ttatttattt atttattaat atttgcatta ttcatatcaa ctacttctta gcataggtgt   120
caagataaat taaagtgttg gcgttgccaa cttcaagcag agaaagatca agtggccttg   180
actgtaactt tttgactgga tcatcaagtc tattattttg ggaatttatt gaaatatact   240
gataatataa ataattttta tattaccaat taattagagt ttgttatatt attataaaat   300
t                                                                   301

<210> SEQ ID NO 108
<211> LENGTH: 301
<212> TYPE: DNA
<213> ORGANISM: Glycine max

<400> SEQUENCE: 108
aatttgcagt tagtgctaca agagtgagct tcacgatgac gaggagtctc tcccatattt    60
```

```
gtcgttgaat atttgtgaat tgcggatcac cacacgacca tttccttccc tctttgttgc    120
cttcttgaca tcttttgttg ctgcaacact cattttttt caattaacct tttcttcctc     180
aacgaagttc aattcttctt tcttttgcac gtaagttgga caattcaatt caattatctt    240
cgtagcgggt tttcttgtgt ttcaaactgg ctaggtggtg gttcttgtaa aaagctagct    300
t                                                                   301
```

```
<210> SEQ ID NO 109
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 109
gtattattag canaatgcct ctatgcaaaa cctttggtct tatgaattgt gttatgtttc    60
acttcaacga acaagaaaaa cactcattat tctccagacc agtaaaagta acaatggtct    120
caattctcaa actcagcaag aaacgcttca aacgtcctag aaagcaagcc attatgacca    180
tcataatcaa accaaaaagg ttacaagtgt atcagctttt gaacagagtc cactcggctc    240
aaagtgaaga aattttaaac acttacacgt cctctgcact ttttttcgact tttnaatcca   300 a                                                                   301
```

```
<210> SEQ ID NO 110
<211> LENGTH: 301
<212> TYPE: DNA
<213> ORGANISM: Glycine max

<400> SEQUENCE: 110
gaagaaaact tacaaagtga aaatatatt tcaaaaagtt attatttcta cattattaga     60
gttatttatt tagaggccat tcgaatgaga tgttttgcaa acaagcgttg gagaaaatag    120
agtcgactat gtatttgagc aaaaaactat aagcagtact ttcttttacc aaatgctcat    180
agcaaaagga aactgtgggg aaatgattct tggggttagt ggttacaaaa ataagtaaat    240
aactgccctg gtgcagttgt aaatctaaca agagatatct ctaaatgaag agtttcatta    300
t                                                                   301
```

```
<210> SEQ ID NO 111
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 111
aaaataaatc ctatgaataa taacttattt gctgttgctt ttgtaatgtt ataaaagctt    60
ttttctttcg gacgcttttt ttatttgccc ttttttgcaca gcacttgcca atttatggaa   120
tagcccgtga gatctgtaat tttctgtatc ccttccccac attggagaac taggctaatt    180
tatatccatc tcttagactt tgtacgaaat cgaaatgcaa ataaataatg agaaatcata    240
gatgcagagc ctactaantg tatatattag taattattac tatagtgcca acaaaagcaa    300
a                                                                   301
```

<210> SEQ ID NO 112
<211> LENGTH: 301
<212> TYPE: DNA
<213> ORGANISM: Glycine max

<400> SEQUENCE: 112

| | |
|---|---|
| attatttgta agggctggat cctttgaata attactccta taaagactgg gctgatctta | 60 |
| tataagaaat atgttaaatt ataaatttct acaagtatta ctgcaatttt atgagaattt | 120 |
| gttttctat tgtaaattgc aatatattcc cccggatccg gaatagcctc atattgactc | 180 |
| caaatagtca tgacaaatga agattgaggc gggatttggc atttttaaac cactgctagt | 240 |
| gcttggtttc cattttggtt gcaagtgtaa ccaaccagct attaaagata caattggaag | 300 |
| a | 301 |

<210> SEQ ID NO 113
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 113

| | |
|---|---|
| tctcctcgat gagatccagc ttctcccttt cctccacggt ctgaggcagt ctccctactg | 60 |
| agaagtgcag aggttgcagt gggcggtgtt gatgagctcc catggcattg ggctgaggca | 120 |
| taccatcaaa tgtcggtccc tcancggtga atgtggagta tagttcaaag tcacccacaa | 180 |
| catgatctcg agggtcttca tagggttccc ccataggctg agggatgggt gtacgtccca | 240 |
| antggggttg ctggccctca aaggaatgg gaaggagtg gttggcgttc tcggtgggca | 300 |
| t | 301 |

<210> SEQ ID NO 114
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 114

| | |
|---|---|
| ctcctcgagg ccaccatcat tnggatcaaa atattccggt ctacctatcc tagaagttat | 60 |
| tgtcctggcc tcccatccac gtgcgtgttt tttcaagcnc caaacaacac cttgtgttgg | 120 |
| tgcttcttgg cagngcatcc gaccnncttt tcggctgccn tttctagcga cagactcacc | 180 |
| ggaccgaggc gcacaaagtg tctcaccta ttttgggcca ttctgagatt ctttcctttg | 240 |
| ccgtaccta ttttagttca cgttgtttgg tcattgtttt gcccttgttt tcaagttcga | 300 |
| c | 301 |

<210> SEQ ID NO 115
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 115

```
tgctatggta gatcagtaag gaaccaagta ntattnacct ctaatgcttt aatctttgca    60
ttcatagctt caatccagtt aggatcttta gaggcnacan tgtatgattg aggttcaact   120
tgttgtgtaa caaacaagat aaccttttga taggaagtag atagtctgtt ataagaaaga   180
acagaacaga gaggataaag agtagtacct gtagagagat tggcaacaat tgatgatgga   240
tatgtgatgt gaaagtcttt tatacttgct tggcctttgt ctctgtctca ttggccttct   300
a                                                                   301
```

<210> SEQ ID NO 116
<211> LENGTH: 301
<212> TYPE: DNA
<213> ORGANISM: Glycine max

<400> SEQUENCE: 116

```
acttgtaact aactaagcta actctagtta caatgtgatc aatctgaatt aaccattatc    60
aaaacagtat ctatgctaag acatagcttg ccttaattgt gacctctttg gaggttgcct   120
taattgcagc agcctagagg gggtgtgttt aggccacatt gcctacaaat atggcctaga   180
tagtgcttac aaggcttggg taatcctcac attacaatgc ggtgttttgg agctgagata   240
ggttctaagc tcaaattcta agagattttg gtggcctgaa gactgaacaa cattttctgc   300
t                                                                   301
```

<210> SEQ ID NO 117
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 117

```
ttatttgttt cttccttttg ctgctgactt ataattgaag gagtttctgc tgtgtttgtg    60
tcatcccgcg aaaagagagc ctcacatttc tgggctaatt tcttttttgcc cccncctttt   120 cgggaataca ccagccagga gttatttggg catggtgtgt ggccttttgg gcttgctttt   180
tggggagcaa atgttttttgg aggggtgtaa atatcacagc ccaagtccac taggctttcc   240
acctccttgt cacgtgcctt ttgtctccca tatttaaaac tgccgagctc ttcaacgttc   300
a                                                                   301
```

<210> SEQ ID NO 118
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 118

```
aaaaantaaa ttctaaaatg gttttttgaa aaatcgtctt agaatgcata tccttttaag    60 atggtttta acaacgaacc gtcttagaaa agtatcattg taagacagtt tttaccaaag   120
aaccgtctta gaatgatatc tttttttcta agacggttac ttaaaaacta tcgtaaaaag   180
taaagacttt ttataatgtt atctacgacg aaggttaata atcgtcgtca aaggtctctt   240
ttaaccgaca taaaaagcgc tttgtgtaac agtgcatatc cataatttat acccgtttat   300
``` a 301

<210> SEQ ID NO 119
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 119
gtcccttgtc attgcctaat aaattaaggt ggcttcattg ggatcaatgc tttcttaagt     60
cttttctaac taacttttgt gttgaacaac ttgtagttct ttggatgant ggttgcaagc    120
ttaaaaagct ttgggatggg gttcaggtat gcatgttgct atacataata caattttctt    180 tcaattttt atggcatggg tacaagagag agtcctaagc ggtaattggt ttcatgttgc    240
ctcaagtgaa gctcattcct aagagcaagg gctacactta ggatgttttg cttctattta    300
t                                                                   301

<210> SEQ ID NO 120
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 120
ataaatgaaa aaaactaatt attattgtat taaaaaatta aataataat tatctttaga     60 taagtttttt nttctcacac aacaattatt ataggacaaa gactgtactt gtagggttat    120
gcaaacgagt ctgacttcct agtttaaaaa atgaggttgg ccttggaacc tctgaggtta    180
gaagcctccc caagtctcga agtgcatgac aaatcaagga gtggccttga atgtataccc    240
ttactaggca ttgttaaacc ctagggaagc gtgataaagg ggaagggaaa tggttaggag    300
a                                                                   301

<210> SEQ ID NO 121
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 121
gaganaggct agcgcttgtc tggcttgtgc ctcttgtccg gcttgtgcaa gtcagccttg     60
gngtttattt tgcacttgtc acgcttctat ctggcttagt ggacttcatt ctgtaatctn    120
gacaatgctt ccatgtggat gtagcccttg gctcactcgt gcagctagtc catgcaattg    180
agtggtcttt tgcacaaaact atctgtgaac ttgtcgagga ataatgtgag gagcattgaa   240
tggaacacta cctcggggta agatttcgga tctggacggt tgtgcgccca aatctgccca    300
t                                                                   301

<210> SEQ ID NO 122
<211> LENGTH: 301
<212> TYPE: DNA
<213> ORGANISM: Glycine max

<400> SEQUENCE: 122

| | | | | | |
|---|---|---|---|---|---|
| caataaatat | aagattgact | taattaatga | taaagaaaaa | aaaagaaaa | aagttatgaa | 60 |
| tttaaattct | ccacaaataa | aaattaataa | ttaacttta | tggatctaaa | aaaaattacc | 120 |
| tcatagactg | tgccatcacc | caactgaaca | agggtaaaaa | gctttctgtc | tgtagtgctt | 180 |
| gcagccacag | aaagtaacca | tggagcataa | acagacattg | tagaaagctc | tggaccctca | 240 |
| ttaccagcag | aatgggacgt | taatattcct | ttcttcattg | catggaaagc | cccaatggcg | 300 |
| a | | | | | | 301 |

<210> SEQ ID NO 123
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 123

| | | | | | |
|---|---|---|---|---|---|
| ggggtatgcg | aggctacnga | gaggggaagt | agggaaaaat | gatgaaggct | aggatgtgga | 60 |
| cggctccgga | gacctttgcg | gtgctctagg | agtttctcct | cctgaagatg | ggccaagtcg | 120 |
| gtggcatgca | ccagcgtcaa | cggctanaga | gcttggaatt | cangccggat | gtccgattcg | 180 |
| aggcctgaga | tgaagcaacn | tagaagtgat | gatggtgaca | acccaacaat | gcgattggcg | 240 |
| agtgcttcaa | attgagccag | gtattctctc | antgaatctt | tctgggttaa | tttaaagagg | 300 |
| a | | | | | | 301 |

<210> SEQ ID NO 124
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 124

| | | | | | |
|---|---|---|---|---|---|
| aggtatcgtg | gcctgttgat | tctccttttt | gtcccttgtt | cttcttcttc | atttggttct | 60 |
| aatattgatt | ctgagttttg | ctttgtaatt | gttgactctg | ttttcataac | acctaattaa | 120 |
| attaaatata | ctcttatgcg | acttttggtg | tacaaaattc | atcatgagct | ccttcgtcat | 180 |
| ttcaagggct | cttcgaaagc | tnacaagcgt | cttattctca | ttggtatcta | tctccatctc | 240 |
| tctctttctc | tctctctctc | tctctcaata | tatatattaa | aataaaagaa | aaattgccat | 300 |
| a | | | | | | 301 |

<210> SEQ ID NO 125
<211> LENGTH: 477
<212> TYPE: DNA
<213> ORGANISM: Glycine max
<220> FEATURE:
<221> NAME/KEY: unsure
<222> LOCATION: (1)..(477)
<223> OTHER INFORMATION: unsure at all n locations

<400> SEQUENCE: 125

| | | | | | |
|---|---|---|---|---|---|
| accttgcaac | atataagaca | gatagcacaa | gaatcaagtg | gagaaattca | gtatggtggc | 60 |
| ggacaccaac | ttgctgtttt | aagaacattt | agccacagac | tttgcaggta | attaaggcag | 120 |

```
actttaatgt ccttggtagt tcgaaccaat gcattgtgca ttttagttat tgacttggca    180
ttttaaactt gatgtaatta agtagtagtt tgttcattaa ttattctnat tcttgctaaa    240
attcaagctt gtncattacc attgcttcat aattactatg ttttattgaa attgcattcc    300
ttagggcctt taatgatgtt gtgaatgggt ttgttgatga tggctggtca ctgatggggt    360
ggaagatgta actatagcca aaaactcatc tccaaacaaa ttttgggat  ccaattacaa    420 tgcatcaatg tttccagcat ttgggggtgg ggtcttgtgt gtcaaggcat caatgct      477
```

<210> SEQ ID NO 126
<211> LENGTH: 301
<212> TYPE: DNA
<213> ORGANISM: Glycine max

<400> SEQUENCE: 126

```
ttttacttaa catggtatct agagtctaac tgagggaata atgaaaatca tgccccacca     60
agaacctaca agatagtagg tccccgatgg atctttctac tcatctccct tcttttggca    120
acttgtttct gcattccgat ggacccttt  tgctcgttgt tgaacaacaa cctttttcatg   180 cttttctggc caccatcgtt tgtcattatt gaaacttcag caacctatcc agactctaac    240
catcaaatct ggtgcacctt tggccgacct gtctagattc aaccaccgca agtcaattgg    300
a                                                                   301
```

<210> SEQ ID NO 127
<211> LENGTH: 902
<212> TYPE: DNA
<213> ORGANISM: Glycine max

<400> SEQUENCE: 127

```
atggacaagt ttaatctcac cttttacaat ggtttgtgat gacattagga aagacctaca     60
gtaacatgtc ctgtatttac tgtgtattat tttaaattct tgatatccgg ccctcatatt    120
agaagggatc cttacggaag gaaagtttta tgtggtcttg ctcgtaggcc aagtaaacgc    180
aaaaacgtat gaaagatcaa gaaggaaat  ccagaaaata tgtcatttga taaacctaat    240
tgaacccatt ttctatattt tccttttcctg cccaaatatt tatgtataag cttccttcaa   300
cttgtctaca tctctgtcac tttatgactg cccttttatag catctccaat aatgaacatc   360
atttagtttt tttaactctt ttaatggctc ttaccatccc acatcggttt taagaacttt    420 agcaacttt  cactccaatg atgcatctct gtaagaactt aaacaggtct caagtttttt    480
acatcttaat ttttctttaa tgggtctcag acgttacctt tcaattgttt tttaatggtt    540
aagagtcagt tctttttataa gaacagttct tactcgtaat gtccatatca tcttcctcca   600
gtggtgaacc tagttaaaaa tggttcttaa ctttaagaac ctacacaaga actatcttag    660
agatgctctt gtagtgaagg tataggttgt tctaagatgg tcacatcaat cacagatcac    720
cttatgtgtt ctatattag  aatttacctt gtctgttaca tcttaaagac gatactgaat    780
tactgatgct tatgcagttt gaggatgatg tgtacttgcc aacggatgag ccacatgggg    840
caattcaagc tagtatgagc cgcttgtgtc aaagctgtag aaactgcagg catacaaggt    900
tg                                                                  902
```

<210> SEQ ID NO 128
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 128

| | | |
|---|---|---|
| tagtatgact aagattaaaa aaaaaaagaa gtcagtggaa gattttttcaa attgaaataa | 60 | |
| aaaaaatacg aatcttctac tccttaaaga atttgggaaa aggggtagag tgattataca | 120 | |
| tgcatttgaa ataaaaaaac acacacgcca aagagcccgt taatattggc cacagggtgg | 180 | |
| tgttgacgag ttataactat atgccttgaa ggaaagaagt tttttttttn aaaaaaaaaa | 240 | |
| aaaaaaagc caaatggtat tataaacaac aaacaaagca caagtagtgc ctaatacaag | 300 | |
| a | 301 | |

<210> SEQ ID NO 129
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 129

| | | |
|---|---|---|
| aacacaacat gaactatttta tacttcacat ttgctcacgc atttcatcaa ataagttgta | 60 | |
| ggcaagttgg ttaaatactt aaatcccaaa agtcctaaca accagcccaa cacaaggcat | 120 | |
| caactaccat tcaacatcat gtaggacaag tgaacaaagc acagtagatt aggtgggaga | 180 | |
| aggacatacc tacggacacg acagagcgtg acaaataacc accaggacat gatgatgagt | 240 | |
| gtgcattttc agtttgcgag gtggaccttg cgncggagag tgttttggca ggctggagaa | 300 | |
| g | 301 | |

<210> SEQ ID NO 130
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 130

| | | |
|---|---|---|
| aattgatgct tctaagttct aatcgcactt caacacngaa atttaggagt gacgagaaat | 60 | |
| agagccctac tttctttctt gccgcgtttt atataataat ttgggttgtg aaagttgggc | 120 | |
| ttggacngng gaacacagat gncccacaac aaatgggccc taatgagaa agaaaatgtg | 180 | |
| gcccaggtca ctttaaaaaa aggaaaagga aaggaatac tgccaatcaa aataaaataa | 240 | |
| aataaagtan attgatanca tgggctaaca tgtcttgccc cattacaagt ccttttttt | 300 | |
| t | 301 | |

<210> SEQ ID NO 131
<211> LENGTH: 301
<212> TYPE: DNA
<213> ORGANISM: Glycine max

<400> SEQUENCE: 131

| | | |
|---|---|---|
| taatgctctt aggcgtattt ttcgtttatg ctacttttat aacatcgaac attttttattt | 60 | |
| tcttttagga gaaagaaaga aataaggtcg ggatatgcct ttggctgtct gtttgtaagc | 120 | |
| atgcatgcat acatccggcc ggtgctggag aatatttgct tatcaccatg gcacaaacgc | 180 | |

```
attattcatt attttcccct ttttaccaac ttaaaacagt ttcttatatt atcgagtttc    240
atagatataa tcatttcagt taagcttaaa aaattggaga atctctataa tttaaattga    300
t                                                                    301

<210> SEQ ID NO 132
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 132
tttcttaaat ctaacaatgt tgncttaatc tccaagatgg tttggaccat catggtctct     60
attaatctcc acatgacacc taattaagta ttattaattt tttcttgtaa attaacaaaa    120
tngagtacat gtcaattaag attattcaag gcaatagaca ggtagtggtt ccaaactact    180
tatctatatc ctaagacaac anaaatctan attgagcata taccttgtcc tcgataaggg    240
gagagtcatc agcaaaccat gtctcctgtc tctcagactg acaatgagca aaacaagaat    300
t                                                                    301

<210> SEQ ID NO 133
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 133
aatgatggtt ccttatttat atattttatt ttaatataag attattttta atgaaaatgt     60
acaacttaaa ttatttccaa caacatgtta taaggaatta tcttgaaaaa tgaatctaag    120
gtttcaatct cattggatag agtctcacaa gtttcttttc aatacactct acatgaaggc    180
aactcgtgcg gattggcttg acaagcatgg atcatctcat gatgaagctt tttaatttga    240
aatacttatc cacagattat tttagccgat gctntgggga ttatgaggat tcgcgtttag    300
t                                                                    301

<210> SEQ ID NO 134
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 134
actttgcaat gaganaaaaa cgaaccttgt atctgtcagg gatgaagctc aaaaagtcac     60
tctcaagact gtgcaaacac atcaattcga atgagttatg taattaatga tatattgtgg    120
atcatacaaa aaaaatgaat acaagtatag ttcactcgtc actgctcatt ttgtaaatct    180
tcatgcttgg gcttatacgc cctctagaat atcttcaagg tctggaccac cctgatcttt    240
acgttgaagg ttgaaccaat atgccatttt agactttaga gttaagagag agtttacaat    300
g                                                                    301
```

-continued

```
<210> SEQ ID NO 135
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 135
tttctgtatt ttctaaatcc aatcccacct ccaacgaaat gtctatagta ttaggcactg      60
catattgaga gatatgtatt gaatgttggc naaaaaaaaa tgcactcaaa ctttaaattt     120
attaaacgat atagcacang ctttgtcaaa ttctatcagt tttccagcac acagtggtgt     180
tatatctgta aattgggtgg atattatgtt ttctatgtag gtggtatttt agacgtggat     240
gtatggtttg gagaaatatc aagggaggaa atttactata agtgtgctgg aaaactgata     300
g                                                                    301

<210> SEQ ID NO 136
<211> LENGTH: 301
<212> TYPE: DNA
<213> ORGANISM: Glycine max

<400> SEQUENCE: 136
cgtgcttctg aaaaagcctt tttggaacac cttttcctag ttatggaaac gctattccaa      60
aagcattttt ggttatggga tggtccttcc ggaagttgtt aacatataa ttagatttga     120 ttttgttatt ttacagtttt agtaattttt tattttatag atttattctt gatttgtatg     180
gaggatgatt acttcaacaa tatgtcagat gaagttggca tggatatgaa tgtgttaact     240
gattgacaag tgtaccaaaa gtctaaataa taaagactcg aaagttcgag tgtcgatttc     300
c                                                                    301

<210> SEQ ID NO 137
<211> LENGTH: 301
<212> TYPE: DNA
<213> ORGANISM: Glycine max

<400> SEQUENCE: 137
taaccattat tgcattgcca tactgttcag cttctcgtag gatatcttct tttaatcgag      60
cctccatttt ctctacccct tcacgaccaa ttccctgaaa gcacaaattg caatatccaa     120
ttcagagaat ttggcacaaa attgacaaac tgctgtgaaa ttatgaggca ccaaatggca     180
tcttagattc tacttagata agcttcatgc tatatctact tcagcattag catgaatgtg     240
tatatttttt gaaatttccc ctaacctgca gcaaacaaag tgaaggggat ttggccagat     300
t                                                                    301

<210> SEQ ID NO 138
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 138
gccatcgcct ctagcgttgc agttttttgt tttatttttc cctcgccaca cccanaaaag      60
gcaaatgagt tgcaatctnt gggaggaaac ctgacccata ncgaattgaa gaaaagctca     120
```

```
aagtggcaat gtnaagggtc cattnttgtc atcatctctt agtcgaaggc cactatagaa    180
gtaggaagga agtgttcacc aatctttgtg ctccccgaca aacctgtaat ttgccgatga    240
gttttcgacn acaataattg cactcgaaca cttacccctag ccatttagt ttatcatagc    300 t                                                                   301

<210> SEQ ID NO 139
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 139 caaacttta tgtgatatcg aaacgactat tgggcttcaa ttaagtagaa acaaagggcc     60
tacataggat tattagttta ttaaaacatg tgatgtcacg gtgggccaca ngaagcagta   120
acaaaagacc ctcacagtat gggctaatat ttcacgcatt gccgacgtaa cgaggtgtca   180
cctttttcac cgtcttcaac atttagccgg gtcactttaa cccgattaca gcccacaaac   240
ctgaatagaa acctaatgat ttctctagcc aacacggaac tcatcgttta aatttnnaga   300
a                                                                   301

<210> SEQ ID NO 140
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 140
atggatgggg tggcaatggc ggaaggaacg gaagagagtg tggcgtcacg gttacgggga    60
agggngttga agaaaacgga ggtggttgtg gcggctggtc ttttgaagag ttgaaaagag   120
ggggttttgt atatggagat ggaagaagag atacctatgg ttgaagccat ttggagggag   180
gaaatgaaag aagaagaaga agaggaggag gcggcgaggg gataaggcca cgcacctttc   240
tgtctctgaa cttaaagcct tttaaacctc cctgtgctgc gtgcgtatca ctgtgtgtct   300
g                                                                   301

<210> SEQ ID NO 141
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 141
taatctctcc caagtccnga ccaaaccaan caatcctctt gataatnggt cttcagtctt    60
gatactgtaa ttgtctccac tgattgtgaa tcgtgtgcac atcgtagata cagaaatggt   120
tgacttactt caaacacgac gacaggtcct gagtgtatnt ggattttaac taaattaact   180
aattgatngg ttatttctc tttcgcacct tgaataccta tcaccgttcg atttcataga   240
atgccattgc caccattttt tttttatctt ttttaaattt gctctacnga ttttnctcc    300 a                                                                   301
```

<210> SEQ ID NO 142
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 142

```
ttgattataa gatattatat aaattaccaa aatttctatc attaatttga caaagtacta      60
ataacgggtc agaagtgata aggatttata tctcttaatc aagtnntata aggtttgatt     120
cctgcacgtt gatntttgaa tatagaataa atcatgttgg accagagaag aatactcatc     180
ttgtgtgtca tcattccgac caagattaat caccacttcc aacaaaacta cttcatacta     240
atattatcat tagaaaaaaa antaacttaa tgaattttta tgaacaggaa tatagctaca     300
t                                                                    301
```

<210> SEQ ID NO 143
<211> LENGTH: 301
<212> TYPE: DNA
<213> ORGANISM: Glycine max

<400> SEQUENCE: 143

```
ggggcttgac aaactcatca ccccctact tgtcaaggct actacccga atatcagaca        60
atcttcaaca ctggataacc tctttcacct tcaatctagc tcagagcttg ggggcttat      120
gtactgtcca gggtccgcaa aatacatgta gcatcctaca tggcactctg aaacttgtgt     180
catccctcca tgtcaaccca agaacaggag cactaacatt cgatccttat tagctaggct     240
cccccaacca acaggttatc cctaacctct taatatttga atatattgtt accatttat     300
c                                                                    301
```

<210> SEQ ID NO 144
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 144

```
gctgaggtcg aaaaatccga cgattctctg gcgttagagg cttctgctga agatagtgtg      60
aaacatgaca gggntgagga agcacaaagt gcaacaccac ccccaacaga aggagatgat     120
cacaaggtta agcctgctgt tgcagtagaa aagattgaag attctgtgcc atcagatgaa     180
tctgtcgttg cagttgaaga tagtgtaaag gaggagaagg aagtggttcc tgactcacac     240
actatcagtg acattgaacc agttcatcag gcnccatcca cagaacaagc tgtggagaaa     300
a                                                                    301
```

<210> SEQ ID NO 145
<211> LENGTH: 301
<212> TYPE: DNA
<213> ORGANISM: Glycine max

<400> SEQUENCE: 145

```
gtttcacttc tttgagtttt ggatttgttg ttattattat aaggaaaggg tttagaataa      60
```

-continued

```
tcatttgaaa ttataagaaa ggatttaatt gattaaagac aagtgcttta atcaattgtc        120
atcaggtaga atctaagaaa ttgctaagcc tttagttcgt tttaatacat gtggtcccct        180
tatttaaatg tcacttggat atccctcgtg ccctttgttt taagcaaaga taacattatg        240
gtacggaggt cattgtcgcc attttccaag gatgcatttt aatttagttt agataacttg        300
a                                                                       301

<210> SEQ ID NO 146
<211> LENGTH: 301
<212> TYPE: DNA
<213> ORGANISM: Glycine max

<400> SEQUENCE: 146
tccagagctc aacttgttat taggacgtga gataggaaga cttatcagta cgtgagatag         60
ataaaagatg aatgcgtgat ttgttactga aggtgattgc aaatatattt gcaaagatat        120
gggttgaatg tagataaaaa atgaatcaga ttcagaaata actaaatttt ccaaaataat        180
aaaatataaa aagaacgtcg agaatgcaac gtggcttcca acatacatgt tagaacattg        240
ttcttgtgac ttcgaaatat cacctcctta aaaatttagt ctcactcaag gaccaacctc        300
a                                                                       301

<210> SEQ ID NO 147
<211> LENGTH: 301
<212> TYPE: DNA
<213> ORGANISM: Glycine max

<400> SEQUENCE: 147
ctgattagtg tgcgtgtgta gcagctaggt gtcgaatata taaccattgt aatgcattgg         60
aaaatcagaa aatgaaggaa ttcagtttaa atatctattt cttctctctt cctaatcttt        120
atcgagttct ctcttactgg aaaaaggtct tgtattactt tgttttcgtg aaaagtttaa        180
tatcggattt gttggacatg tatacatttt ctatttttct tgtgattttc ataataataa        240
aaaaaaaatt ataattttga ttttaatttt caaattcatg attttaaaac atttgatttc        300
c                                                                       301
```